US011779599B2

(12) United States Patent
Nicolette et al.

(10) Patent No.: US 11,779,599 B2
(45) Date of Patent: Oct. 10, 2023

(54) METHODS AND USES FOR DENDRITIC CELL THERAPY

(71) Applicant: CoImmune, Inc., Durham, NC (US)

(72) Inventors: Charles Nicolette, Durham, NC (US); Mark Debenedette, Durham, NC (US); Joseph Horvatinovich, Raleigh, NC (US); Alex Dusek, Chapel Hill, NC (US); Tamara Monesmith, Cambridge, MA (US)

(73) Assignee: COIMMUNE, INC., Durham, NC (US)

( * ) Notice: Subject to any disclaimer, the term of this patent is extended or adjusted under 35 U.S.C. 154(b) by 689 days.

(21) Appl. No.: 16/762,314

(22) PCT Filed: Nov. 7, 2018

(86) PCT No.: PCT/US2018/059610
§ 371 (c)(1),
(2) Date: May 7, 2020

(87) PCT Pub. No.: WO2019/094458
PCT Pub. Date: May 16, 2019

(65) Prior Publication Data
US 2021/0030791 A1    Feb. 4, 2021

Related U.S. Application Data

(60) Provisional application No. 62/582,853, filed on Nov. 7, 2017.

(51) Int. Cl.
*A61K 35/15*     (2015.01)
*G01N 33/569*    (2006.01)
*A61K 39/00*     (2006.01)

(52) U.S. Cl.
CPC .......... *A61K 35/15* (2013.01); *A61K 39/0011* (2013.01); *G01N 33/56972* (2013.01); *A61K 2039/5154* (2013.01)

(58) Field of Classification Search
None
See application file for complete search history.

(56) References Cited

U.S. PATENT DOCUMENTS

| | | |
|---|---|---|
| 5,199,942 A | 4/1993 | Gillis |
| 8,574,901 B2 | 11/2013 | Schuler et al. |
| 9,079,976 B2 | 7/2015 | Shirwan et al. |
| 2007/0248578 A1 | 10/2007 | Tcherepanova |
| 2008/0311155 A1 | 12/2008 | Nicolette et al. |
| 2012/0114680 A1 | 5/2012 | Pogue-Caley et al. |
| 2014/0140986 A1 | 5/2014 | Santos et al. |
| 2016/0101170 A1 | 4/2016 | Hacohen et al. |
| 2017/0065690 A1 | 3/2017 | Debenedette et al. |

FOREIGN PATENT DOCUMENTS

| | | |
|---|---|---|
| CA | 2874065 A1 | 6/2015 |
| WO | WO-9729182 A1 | 8/1997 |
| WO | WO-0216560 A1 | 2/2002 |
| WO | WO-2006031870 A2 | 3/2006 |
| WO | WO-2006042177 A2 | 4/2006 |
| WO | WO-2007117682 A2 | 10/2007 |
| WO | WO-2015127190 A1 | 8/2015 |
| WO | WO-2016168264 A1 | 10/2016 |
| WO | WO-2017032867 A1 | 3/2017 |
| WO | WO-2019094458 A1 | 5/2019 |

OTHER PUBLICATIONS

Afzali, B and Lombardi, G., "Regulatory T Cells in Renal Cell Carcinoma: Additional Fuel to the Bonfire of Debate," *BJU International* 112(5):538-539, Blackwell Science, United Kingdom (Sep. 2013).

Ajdary, S., et al., "Comparison of the Immune Profile of Nonhealing Cutaneous Leishmaniasis Patients With Those With Active Lesions and Those Who Have Recovered From Infection," *Infection and Immunity* 68(4):1760-1764, American Society For Microbiology, United States (Apr. 2000).

Amin, A., et al., "Survival With AGS-003, an Autologous Dendritic Cell-Based Immunotherapy, in Combination With Sunitinib in Unfavorable Risk Patients With Advanced Renal Cell Carcinoma (RCC): Phase 2 Study Results," *Journal for Immunotherapy of Cancer* 3:14, BioMed Central, United Kingdom (Apr. 2015).

Argos Therapeutics Inc., "Argos Reports Interim Results of the ADAPT Trial and Provides Perspective on Decision to Continue the Trial," GlobeNewswire.com, published on Apr. 18, 2017, accessed at https://www.globenewswire.com/news-release/2017/04/18/961866/0/en/Argos-Reports-Interim-Results-of-the-ADAPT-Trial-and-Provides-Perspective-on-Decision-to-Continue-the-Trial.html, accessed on Oct. 23, 2020, 6 pages.

Basu, S., et al., "Purification of Specific Cell Population by Fluorescence Activated Cell Sorting (FACS)," *Journal of Visualized Experiments* 41:1546, MYJoVE Corporation, United States (Jul. 2010).

Broekman, F., et al., "Tyrosine Kinase Inhibitors: Multi-targeted or Single-Targeted?" *World Journal of Clinical Oncology* 2(2):80-93, Baishideng Publishing Group, United States (Feb. 2011).

Brosierhus, H., et al., "Enrichment and Detection of Live Antigen-Specific CD4(+) and CD8(+) T Cells Based on Cytokine Secretion," *European Journal of Immunology* 29(12):4053-4059, Verlag Chemie, Germany (Dec. 1999).

(Continued)

*Primary Examiner* — Daniel C Gamett

(74) *Attorney, Agent, or Firm* — STERNE, KESSLER, GOLDSTEIN & FOX P.L.L.C.

(57) ABSTRACT

This invention provides methods of evaluating immune system parameters to identify and treat patients who are likely to experience more favorable treatment outcomes. This invention also provides methods for treating a human patient with a dendritic cell therapy by obtaining at least one value or measurement of the level and/or amount of a particular type of treatment indicator in the patient, confirming that said value or measurement exceeds or is less than the treatment threshold value for that value or measurement, and administering said dendritic cell therapy to the patient.

20 Claims, 11 Drawing Sheets

(56) References Cited

OTHER PUBLICATIONS

Calderhead, D.M., et al., "Cytokine Maturation Followed by CD40L mRNA Electroporation Results in a Clinically Relevant Dendritic Cell Product Capable of Inducing a Potent Proinflammatory CTL Response," *Journal of Immunotherapy* 31(8):731-741, Lippincott Williams & Wilkins, United States (Oct. 2008).

Cesana, G.C., et al., "Characterization of CD4+CD25+ Regulatory T Cells in Patients Treated With High-Dose interleukin-2 for Metastatic Melanoma or Renal Cell Carcinoma," *Journal of Clinical Oncology* 24(7):1169-1177, Grune & Stratton, United States (Mar. 2006).

Debenedette, M.A., et al."Priming of a Novel Subset of CD28+ Rapidly Expanding High-Avidity Effector Memory CTL by Post Maturation electroporation-CD40L Dendritic Cells Is IL-12 Dependent," *Journal of Immunology* 181(8):5296-5305, American Association of Immunologists, United States (Oct. 2008).

Griffiths, R.W., et al., "Frequency of Regulatory T Cells in Renal Cell Carcinoma Patients and Investigation of Correlation With Survival," *Cancer Immunology* 56(11):1743-1753, Springer, Germany (Nov. 2007).

Hasan, M., et al.,"Semi-automated and Standardized Cytometric Procedures for Multi-Panel and Multi-Parametric Whole Blood Immunophenotyping," *Clinical Immunology* 157(2):261-276, Academic Press, United States (Apr. 2015).

International Search Report and Written opinion for International Application No. PCT/US2018/059610, Commissioner for Patents, Alexandria, Virginia, United States, dated Jan. 30, 2019, 8 pages.

Jager, J.G.S., et al., "Evaluation of RNA Amplification Methods to Improve DC Immunotherapy Antigen Presentation and Immune Response," *Molecular Therapy* 2(5):e91, Nature Publishing Group, United States (May 2013).

Kammula, U.S., et al., "Functional Analysis of Antigen-Specific T Lymphocytes by Serial Measurement of Gene Expression in Peripheral Blood Mononuclear Cells and Tumor Specimens," *Journal of Immunology* 163(12):6867-6675, Williams & Wilkins, United States (Dec. 1999).

Kammula, U.S and Serrano, O.K., "Use of High Throughput qPCR Screening to Rapidly Clone Low Frequency Tumour Specific T-cells From Peripheral Blood for Adoptive Immunotherapy," *Journal of Translational Medicine* 6:60, BioMed, United Kingdom (Oct. 2008).

Keenan, R.D et al., "Purification of Cytomegalovirus-Specific CD8 T Cells From Peripheral Blood Using HLA-peptide Tetramers," *British Journal of Haematology* 115(2):428-434, Blackwell Scientific Publications, United Kingdom (Nov. 2001).

Lowther, D.E., et al., "PD-1 Marks Dysfunctional Regulatory T Cells in Malignant Gliomas," *JCI insight* 1(5): e85935, American Society for Clinical Investigation, United States (Apr. 2016).

Magro, F., et al., "Intestinal Na+-K+-ATPase Activity and Molecular Events Downstream of Interferon-Gamma Receptor Stimulation," *British Journal of Pharmacology* 142(8):1281-1292, Macmillian Journals Ltd, United Kingdom (Aug. 2004).

Raimondi, G., et al., "Regulated Compartmentalization of Programmed Cell death-1 Discriminates CD4+CD25+ Resting Regulatory T Cells From Activated T Cells," *Journal of Immunology* 176(5):2808-2816, Williams & Wilkins, United States (Mar. 2006).

Romani, N., et al., "Proliferating Dendritic Cell Progenitors in Human Blood," *Journal of Experimental Medicine* 180(1):83-93, Rockefeller University Press, United States (Jul. 1994).

Sallusto, F., et al., "Efficient Presentation of Soluble Antigen by Cultured Human Dendritic Cells Is Maintained by Granulocyte/ macrophage Colony-stimulating Factor Plus Interleukin 4 and Downregulated by Tumor Necrosis Factor Alpha," *The Journal of Experimental Medicine* 179(4):1109-1118, Rockefeller University Press, United States (Apr. 1994).

Schwarzer, A., et al., "Regulatory T-cells and Associated Pathways in Metastatic Renal Cell Carcinoma (mRCC) Patients Undergoing DC-vaccination and Cytokine-Therapy," *PLoS One* 7(10):e46600, Public Library of Science, United States (Oct. 2012).

Steinman, R.M., "The Dendritic Cell System and its Role in Immunogenicity," *Annual Review of Immunology* 9:271-296, Annual Reviews, United States (Apr. 1991).

Stemberger, C., et al., "Novel Serial Positive Enrichment Technology Enables Clinical Multiparameter Cell Sorting," *PLoS One* 7(4):e35798, Public Library of Science, United States (Apr. 2012).

Tatura, R., et al., "Quantification of Regulatory T Cells in Septic Patients by Real-Time PCR-based Methylation Assay and Flow Cytometry," *PLoS One* 7(11):e49962, Public Library of Science, United States (Nov. 2012).

Tcherepanova, I., et al., "Multiplex RT-PCR Amplification of HIV Genes to Create a Completely Autologous DC-based Immunotherapy for the Treatment of HIV Infection," *PLoS One* 3(1):e1489, Public Library of Science, United States (Jan. 2008).

Wierda, W.G., et al., "CD40-ligand (CD154) Gene Therapy for Chronic Lymphocytic Leukemia," *Blood* 96(9):2917-2924, American Society of Hematology, United States (Nov. 2000).

Wolf, A.M., et al., "Increase of Regulatory T Cells in the Peripheral Blood of Cancer Patients," *Clinical Cancer Research* 9(2):606-612, American Association for Cancer Research Inc., United States (Feb. 2003).

Koga, N., et al., "Immunological efficacy of herbal medicines in prostate cancer patients treated by personalized peptide vaccine," *Cancer Sci* 108(12):2326-2332, Wiley-Blackwell, United States (Dec. 2017).

METHODS AND USES FOR DENDRITIC CELL THERAPY

FIELD OF THE INVENTION

The present invention relates to therapeutic uses of dendritic cells and evaluation of patients for the likelihood of effectiveness of treatment with dendritic cell therapies.

BACKGROUND

Cell therapy utilizes modified antigen presenting cells (APCs) or immune effector cells to initiate an immune response in a patient. Antigen presenting cells are important to cell therapy because they initiate an immune response; specifically, they are capable of inducing a primary immune response from T lymphocytes.

Dendritic cells (DCs) are the most potent APCs involved in adaptive immunity. They coordinate the initiation of immune responses by naive T cells and B cells and induce antigen-specific cytotoxic T lymphocyte (CTL) responses. DCs are specialized in several ways to prime helper and killer T cells in vivo. For example, immature DCs that reside in peripheral tissues are equipped to capture antigens and to produce immunogenic MHC-peptide complexes. Immature DCs develop into potent T cell stimulators by upregulating adhesion and costimulatory molecules in response to maturation-inducing stimuli such as inflammatory cytokines and migrate into secondary lymphoid organs to select and stimulate rare antigen-specific T cells. Potent stimulation of T cells occurs only after DC maturation, a process that increases the availability of MHC/peptide complexes on the cell surface in addition to co-stimulatory molecules that direct the effector function of the responding T-cells.

Co-stimulation is typically necessary for a T cell to produce sufficient cytokine levels to induce clonal expansion. One characteristic of dendritic cells that makes them potent antigen presenting cells is that they are rich in co-stimulatory molecules of the immune response, such as the molecules CD80 and CD86, which activate the molecule CD28 on T lymphocytes. In return, T-helper cells express CD40L (CD40 ligand), which ligates CD40 on DCs. These interactions between DCs and T cells leads to maturation of the DCs and the development of effector function in the T cells. The expression of adhesion molecules, like the molecule CD54 or the molecule CD11a/CD18, facilitates cooperation between the DCs and the T cells. Another special characteristic of DCs is the deployment of different functions depending on their stage of differentiation. For example, two principal functions of the immature dendritic cell are the capture of antigen and antigen transformation, whereas the capacity to present antigen to stimulate T cells increases as the dendritic cell migrates into the tissues and the lymphatic system and matures. Thus, the transition of the immature dendritic cell to the mature dendritic cell is a fundamental step in the initiation of the immune response.

In some reports, DC maturation was followed by monitoring changes of surface markers on the cells during the maturation process. Some of the more important cell surface markers characteristic of different stages of maturation of DCs include: CD34+ for hematopoietic stem cells; CD14++, DR+, CD86+, CD16+/−, CD54+, and CD40+ for monocytes; CD14+/−, CD16−, CD80+/−, CD83−, CD86+, CD1a+, CD54+, DQ+, and DR++ for immature dendritic cells; and CD14−, CD83++, CD86++, CD80++, DR+++, DQ++, CD40++, CD54++, and CD1a+/− for mature dendritic cells, where "+" indicates positive expression, "++" indicates higher expression, "+/−" indicates weaker or lower expression, and "−" indicates very weak, low, or undetectable expression. Expression of surface markers and other genes can vary depending upon the maturation process of the cells as well as the methods by which expression is measured, as is known in the art (see, e.g., Hasan et al. (2015) *Clin. Immunol.* 157: 261-76).

For immunotherapy, mature DCs are currently preferred to immature DCs. Only fully mature DC progeny lack GM-CSF Receptor (GM-CSF-R) and remain stably mature upon removal and/or in the absence of GM-CSF. Mature DCs have also been shown to be superior in inducing T cell responses in vitro and in vivo, and can take up and present antigen to T-lymphocytes in vitro or in vivo. Modified, antigen-presenting DCs and/or T cells educated from these modified DCs have many applications, including diagnosis, therapy, vaccination, research, screening and gene delivery.

It is difficult to isolate mature dendritic cells from peripheral blood because less than 1% of white blood cells belong to this category, and mature DCs are also difficult to extract from tissues. This difficulty has driven research and development toward new methods to generate mature dendritic cells using alternative sources. Several methods are reported to produce mature DCs from immature dendritic cells, and it has been shown that different methods can produce mature DCs with different properties.

PME-CD40L DCs are mature DCs that are also phenotypically CD83+ and CCR7+. PME-CD40L DCs can be produced, for example, by a method comprising the sequential steps of: (a) culturing isolated immature dendritic cells (iDCs) with an interferon gamma receptor (IFN-γR) agonist in the presence of a TNF-αR agonist and PGE$_2$ for approximately 12 to 30 hours to produce CD83+ mature dendritic cells; and (b) transfecting said CD83+ mature dendritic cells (mDCs) with a CD40 agonist to produce a transient CD40 signal. The CD40 agonist can be provided as mRNA encoding a CD40L polypeptide; in some instances, this mRNA encodes a CD40L polypeptide consisting of amino acid residues 21-261 of SEQ ID NO:2 of WO2007117682. The mRNA encoding the CD40L polypeptide may be cotransfected with an mRNA encoding an antigen to produce the PME-CD40L DCs.

More detailed methods for production of PME-CD40L DCs include those disclosed in WO2006042177 (Healey et al.); WO2007117682 (Tcherepanova et al.); DeBenedette et al. (2008) *J. Immunol.* 181: 5296-5305; and Calderhead et al. (2008) *J. Immunother.* 31: 731-41. The resulting "PME-CD40L" DCs can be used to treat a human patient having cancer or an immune disease or disorder and also to stimulate the production in vivo or in vitro of advantageous T cells.

PME-CD40L DCs have advantageous properties, including stimulating production of "stem cell memory" T cells ("T$_{SCM}$ cells") both in vivo and in vitro, as described in WO 2015/127190 (DeBenedette et al.) and corresponding US Pub. No. 20170065690 (DeBenedette et al.). T$_{SCM}$ cells are stem cell memory T cells that are multipotent and can also give rise to progeny cells that are themselves T$_{SCM}$ cells. The production of T$_{SCM}$ cells by exposure to PME-CD40L DCs can occur in vivo in human patients having immune diseases or disorders, including AIDS or infection with HIV, and can also occur in vitro when PME-CD40L DCs are cocultured with lymphocytes. PME-CD40L DCs have also been shown to support long term antigen-specific CTL effector function and to induce a type of effector memory CTLs designated Rapidly Expanding High-Avidity ("REHA") cells (see DeBenedette et al. (2008) *J. Immunol.* 181: 5296-5305).

These $T_{SCM}$ and/or REHA cells can then be reintroduced into a patient to help stimulate the immune response of the patient from whom they were derived (i.e., autologous treatment) or to treat another patient in adoptive transfer therapy (i.e., heterologous treatment).

A Phase 3 clinical trial of Argos Therapeutic, Inc.'s ("Argos") PME-CD40L DC therapy for Renal Cell Carcinoma, designated "AGS-003" or "Rocapuldencel-T," began in January 2013 and is presently ongoing. This "ADAPT" trial was designed to evaluate overall survival ("OS") in patients with newly diagnosed metastatic Renal Cell Carcinoma ("mRCC") receiving Rocapuldencel-T in combination with standard of care ("SOC") versus SOC alone. In February 2017, an interim analysis was conducted by the Independent Data Monitoring Committee ("IDMC") and found that the hazard ratio was 1.10, which was greater than the pre-defined futility boundary for the final interim analysis of 0.98. The IDMC therefore recommended that the study be discontinued for futility. Argos conducted extensive analysis of the available data from the study and, after consultation with the FDA, decided to continue with the clinical trial (see Argos Press Release dated Apr. 18, 2017).

SUMMARY OF THE INVENTION

Surprisingly, the instant inventors have discovered that patients having certain immune system properties are more likely to experience favorable treatment outcomes from dendritic cell therapy. The invention provides methods of evaluating immune system parameters such as, for example, regulatory T cell ("Treg") counts for use in helping to identify and treat patients who are likely to experience more favorable treatment outcomes.

For example, patients having high levels of Treg cells are likely to benefit from dendritic cell therapies. Treatment of these patients with an effective dendritic cell therapy produces an immune response, part of which is a decrease in the numbers and/or levels of Treg cells in said patient. Such patients may benefit from dendritic cell therapies more than other patients having lower levels of Treg cells.

In some embodiments, the dendritic cell therapy used to treat the patient comprises PME-CD40L mature DCs that are loaded with an antigen. In some embodiments, the DCs are loaded with an antigen by transfection with RNA encoding said antigen. In some embodiments, the RNA encoding the antigen is prepared from cancer cells of the patient (i.e., the antigen is "autologous" to the patient).

Thus, the invention provides methods for treating a human patient with a dendritic cell therapy comprising obtaining at least one value or measurement of the level and/or amount of a particular type of treatment indicator such as, for example, an immune cell and/or serum chemistry marker in the patient; confirming that said value or measurement exceeds or is less than the treatment threshold value for that value or measurement, as appropriate; and administering said dendritic cell therapy to the patient. The invention also provides methods for administering a dendritic cell therapy to a patient comprising obtaining at least one value or measurement of the level and/or amount of a particular type of treatment indicator; confirming that said value or measurement exceeds or is less than the treatment threshold value for that value or measurement, as appropriate; and administering said dendritic cell therapy to the patient. In some embodiments, the methods comprise obtaining two, three, or four values or measurements, confirming that the treatment threshold value has been met for each, and administering said dendritic cell therapy to the patient.

In some embodiments, the invention provides a method for treating a human patient with a dendritic cell therapy comprising obtaining a count of the Tregs per unit volume in the blood of said patient; confirming that said count exceeds a treatment threshold value of Tregs; and administering said dendritic cell vaccine to said patient. In some embodiments, the treatment threshold value is Tregs per unit volume of blood of at least 500 Tregs/100 microliters of patient whole blood, or at least 550, 600, 650, 700, 750, 800, 850, or 900 Tregs/100 microliters of patient whole blood. In some embodiments, the method comprises determining the percentage of CD4+ cells that are Treg cells, and the treatment threshold value is at least 1%, 1.5%, 1.75%, or 2% or higher.

In some embodiments, the treatment threshold value of Tregs is measured in a patient prior to any therapeutic and/or pharmaceutical treatment for a disease or disorder such as cancer or an immune disease or disorder (herein referred to as "baseline"). In some embodiments, the threshold value of Tregs in a patient is measured after one or more therapeutic and/or pharmaceutical treatments for a disease or disorder.

In some embodiments, treatment of a patient with a dendritic cell therapy stimulates an immune response as measured, for example, by a reduction in the number of Tregs per unit volume in the patient's blood. The invention also provides methods of evaluating the stimulation of an immune response in a patient following treatment, such as, for example, detecting an increase in cell populations such as Treg/eff cells as further described below.

Figure 2:
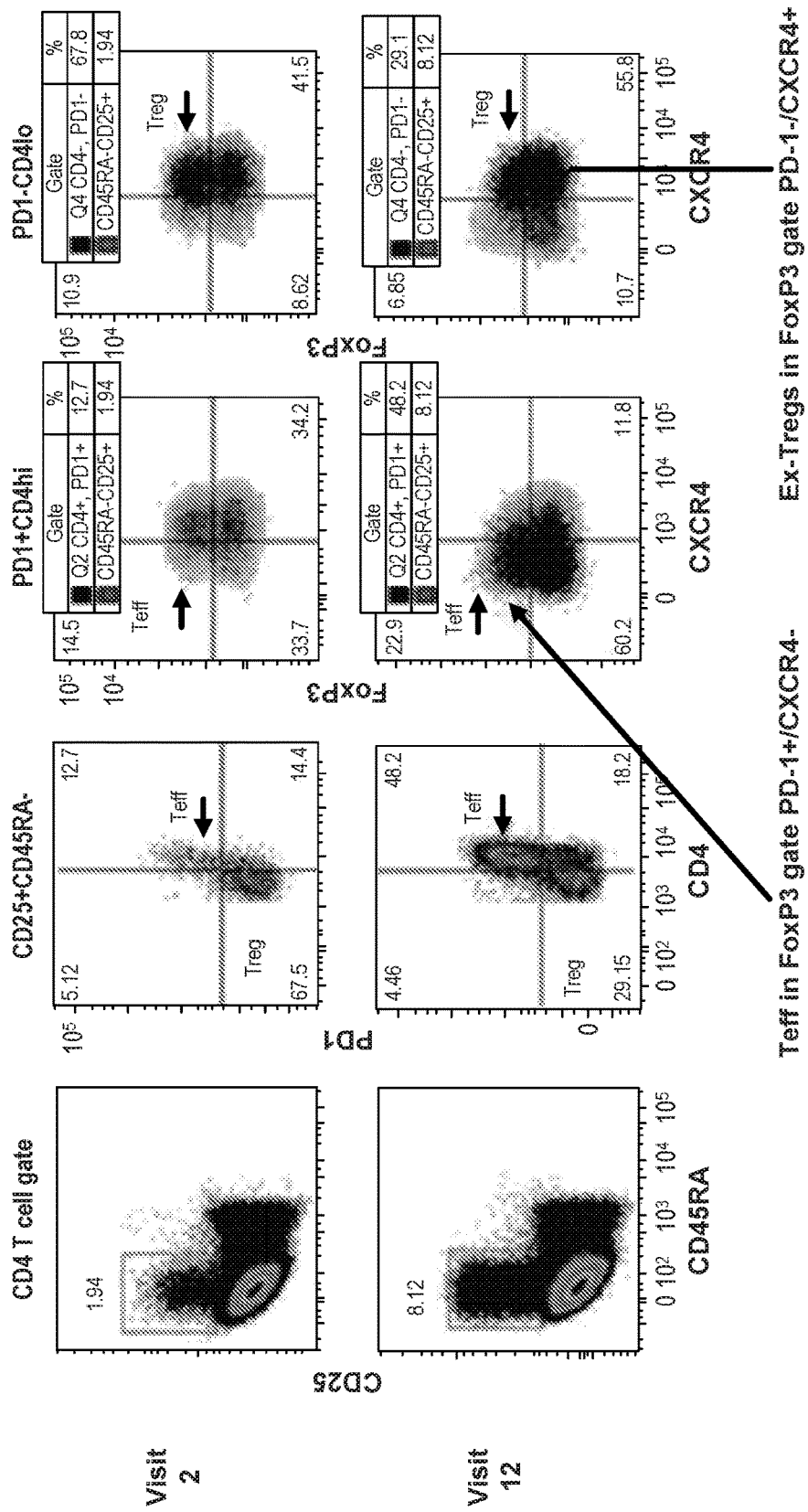
FIG. 2 shows in vitro detection of Foxp3+/CD25+ Treg subsets by PD-1 and CXCR4 expression. Cells are quantified using multi-color flow cytometry. This method determines an absolute number of cells per volume of blood or tissue culture medium. PBMCs were collected from a patient enrolled in the AGS-003 clinical trial at visit 2 (prior to the administration of AGS-003) and at visit 12 (following the $7^{th}$ administration of a dose of AGS-003 to the patient). The PBMCs were cultured for six days in Xvivo media containing 10% AB serum; no additional stimuli were added to the cultures. On day 6, PBMC cultures were stained for flow cytometry to determine the number of activated FoxP3+/CD25+/CD4+ T cells. First, CD4+ T cells were gated to identify CD25+/CD45RA− T cells, as shown in the boxed areas in the leftmost panels of FIG. 2. These CD25+/

CD45RA− T cells were then further gated to determine their expression of PD-1 and their level of expression of CD4 (see FIG. 2, second set of panels) so as to distinguish Treg from Treg/eff cells, with PD-1−/CD4 low-expressing (Treg) cells shown in the lower left quadrant and PD-1+/CD4 high-expressing Treg effector cells (Treg/eff) shown in the upper right quadrant of these panels. Each of these Treg/eff and Treg populations were then subgated by expression of FoxP3 (y-axis) and CXCR4 (x-axis) as shown in FIG. 2 in the third and fourth sets of panels from left, respectively. The third set of panels shows that the PD-1+/CD4 high-expressing/FoxP3+ cells are CXCR4 negative (FIG. 2, third set of panels, upper left quadrant). The fourth set of panels shows that the PD-1−/CD4 low-expressing/FoxP3+ cells are CXCR4 positive (FIG. 2, fourth set of panels, upper right quadrant). As shown, this gating strategy can be used to identify the two FoxP3+ subsets of the CD4+/CD25+/CD45RA−/FoxP3+T regulatory cells: Treg/effs (FoxP3+/PD-1+/CXCR4−) and Tregs (FoxP3+/PD-1−/CXCR4+), shown in the third and fourth set of panels, respectively. As demonstrated by this data comparing pre-treatment PBMCs to PBMCs from the same patient after administration of 7 doses of AGS-003 dendritic cell product, AGS-003 treatment can increase the numbers of Treg/eff cells after in vitro culture expansion.

Figure 3:
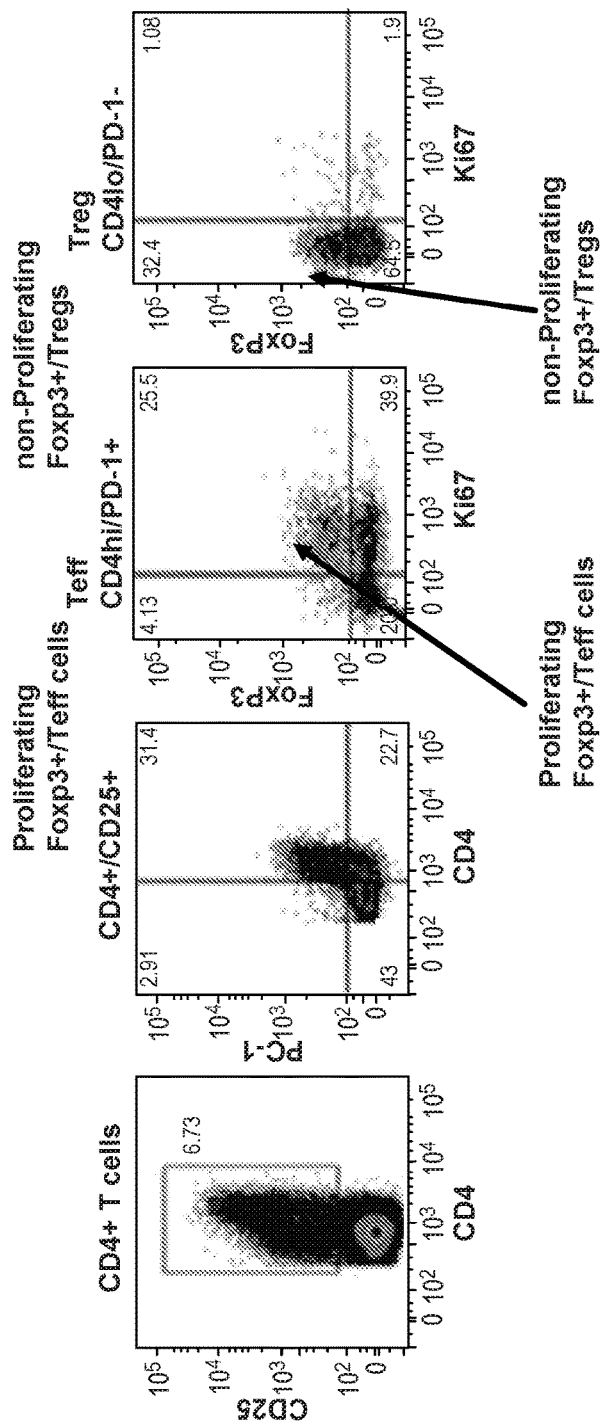

FIG. 3 illustrates the differentiation of classic Treg cells and Treg/eff cells by the combinatorial expression of PD-1 and CXCR4. Classic Treg cells are PD-1−/CXCR4+ and Treg effector cells are PD-1+/CXCR4−. FIG. 3 shows that CD4+/PD-1+/FoxP3+ T cells proliferate in vitro when stimulated with AGS-003 DC product. PBMCs collected at the patient's visit 1 (baseline) were cultured for six days in Xvivo media containing 10% AB serum at a 10:1 ratio with autologous AGS-003 DC product. FIG. 3 shows cells that were first gated for expression of CD25 and CD4 to identify CD25+/CD4+ T cells (first panel, boxed area); these cells were then gated by expression of PD-1 (second panel) into PD-1+(second panel, upper right quadrant) and PD-1− T cells. Cells were then examined for FoxP3 expression and expression of the cell cycle marker Ki67 to determine proliferation (FIG. 3, third and fourth panels). Treg/eff cells were shown to be proliferating (FIG. 3, third panel, upper right quadrant, showing that CD4+ high-expressing/CD25+/FoxP3+/PD-1+ cells include Ki67+ cells), whereas most of the Treg cells were not (FIG. 3, fourth panel, upper left quadrant, showing CD4+ low expressing/CD25+/FoxP3+/PD-1− cells include mostly Ki67− cells).

Figure 4:
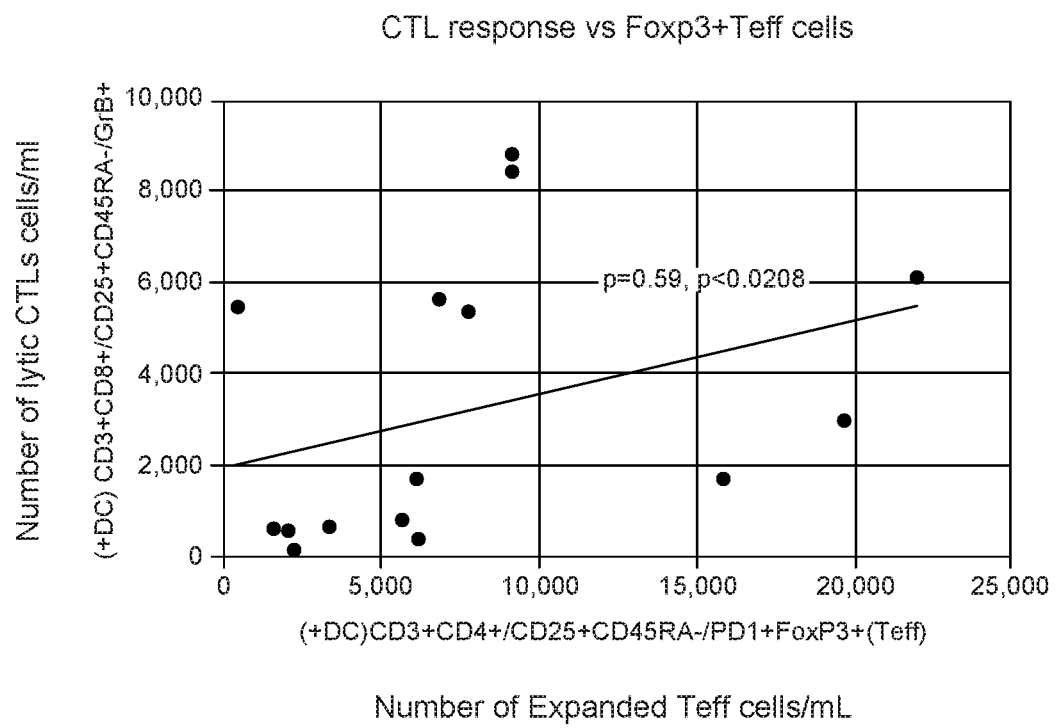

FIG. 4 shows the concurrent expansion of Treg effector cells and CTLs after in vitro culture of PBMCs with AGS-003 DC autologous product. PBMCs were collected from 15 ADAPT clinical trial subjects at baseline and cultured with autologous AGS-003 DC product for 6 days. On day 6, the number of CD3+/CD8+/CD25+/CD45RA−/Grb+ CTLs (y-axis) were determined and plotted versus the number of CD3+/CD4+/CD25+CD45RA−/PD-1+/Foxp3+ Treg effector cells (x-axis). A statistically significant association was detected between the number of CTLs and Treg/eff cells in the cultures ($\rho=0.59$, $p<0.0208$).

Figure 5:
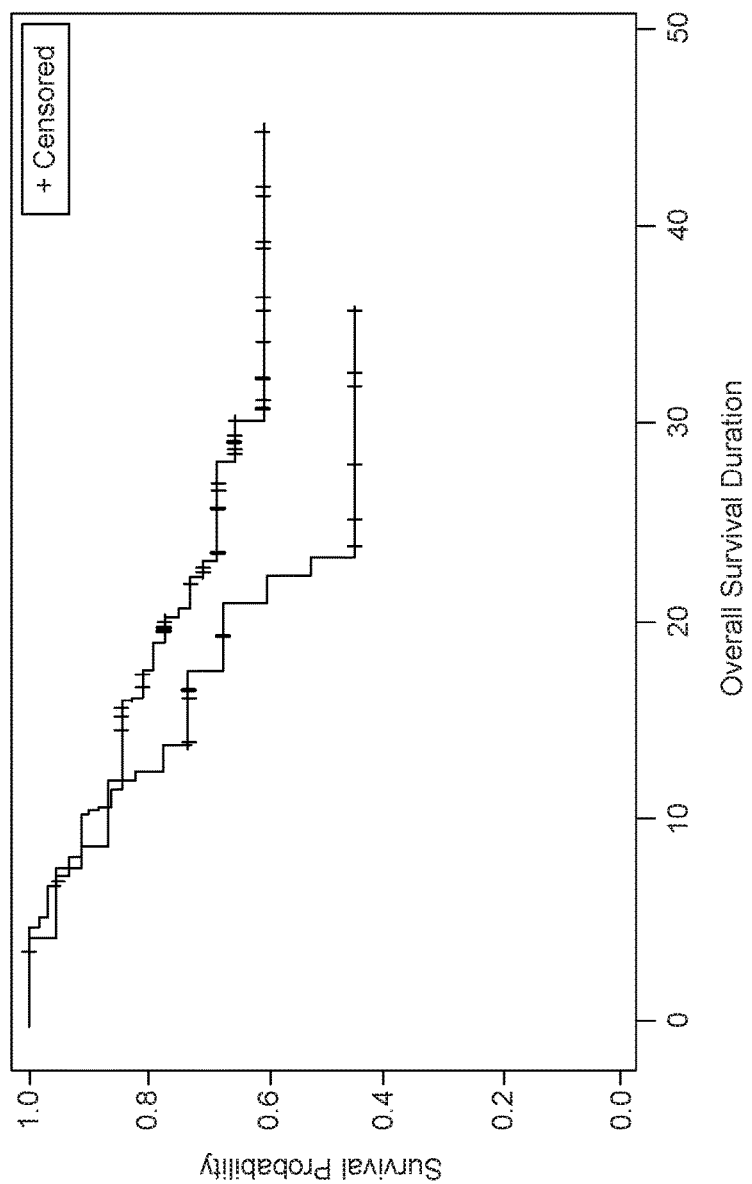

FIG. 5 shows a Kaplan-Meier plot of overall survival of patients enrolled in Argos' ADAPT clinical trial who had baseline lymphocyte counts in the highest quartile. The hazard ratio of data from patients in the combination treatment arm (AGS-003 with standard of care, upper line) to the data from patients in the Standard of Care arm was 0.5999.

Figure 6:
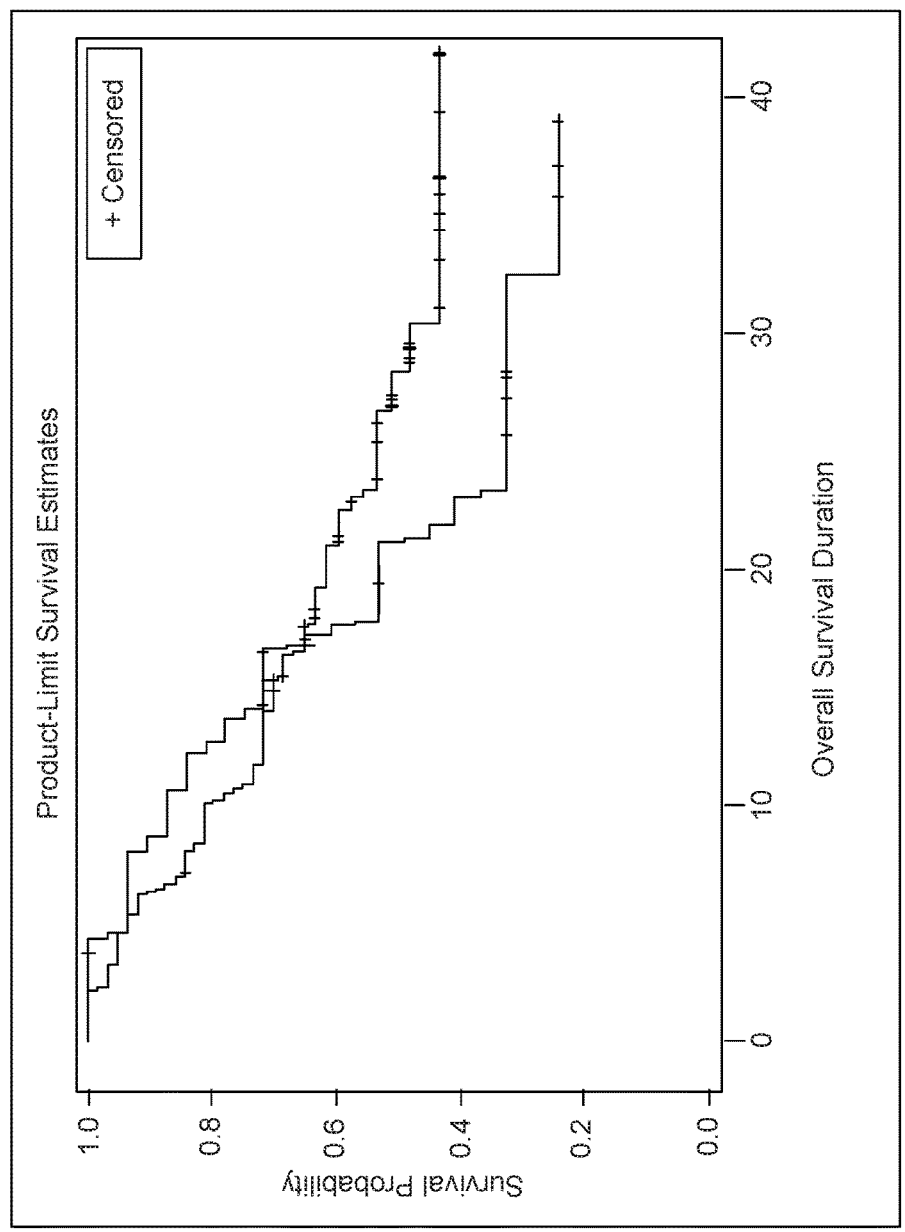

FIG. 6 shows a Kaplan-Meier plot of overall survival of patients enrolled in Argos' ADAPT clinical trial who had baseline lymphocyte/monocyte ratios in the highest quartile. The hazard ratio of data from patients in the combination treatment arm (AGS-003 with standard of care, upper line on right side of graph) to the data from patients in the Standard of Care arm was 0.7356.

Figure 7:
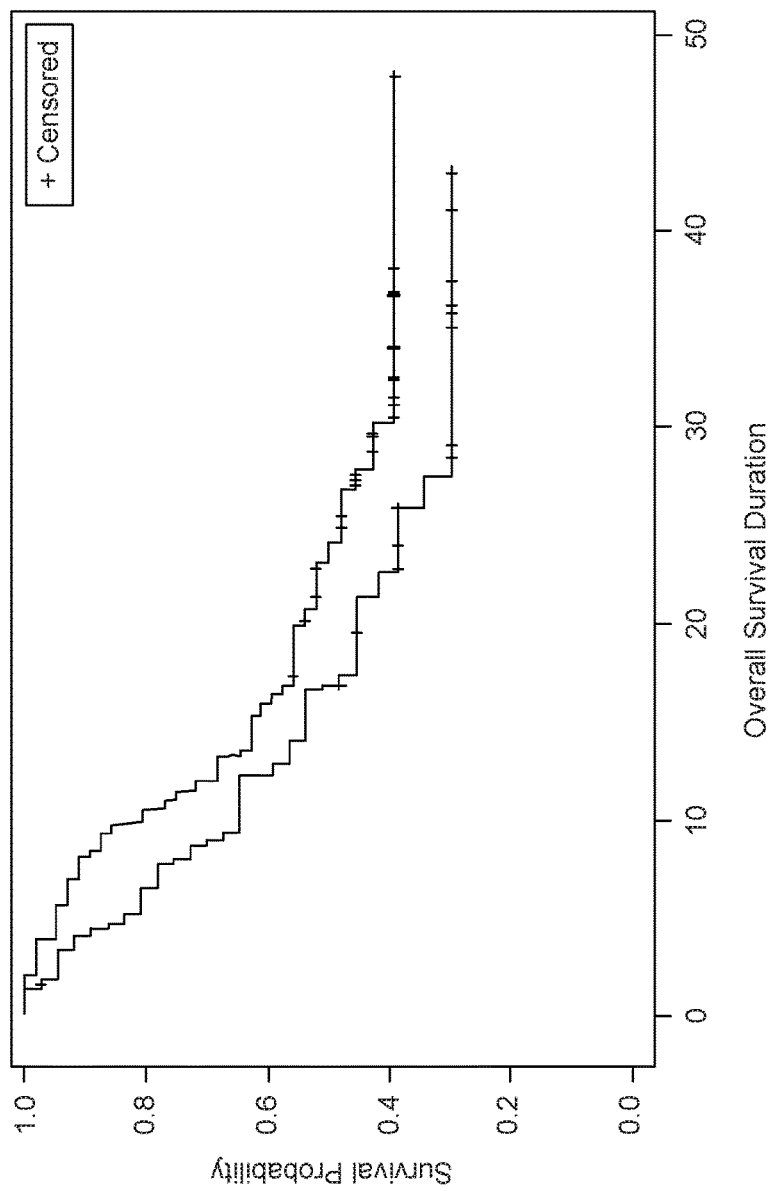

FIG. 7 shows a Kaplan-Meier plot of overall survival of patients enrolled in Argos' ADAPT clinical trial who had baseline C-reactive protein values in the highest quartile. The hazard ratio of data from patients in the combination treatment arm (AGS-003 with standard of care, upper line) to the data from patients in the Standard of Care arm was 0.7164.

Figure 8:
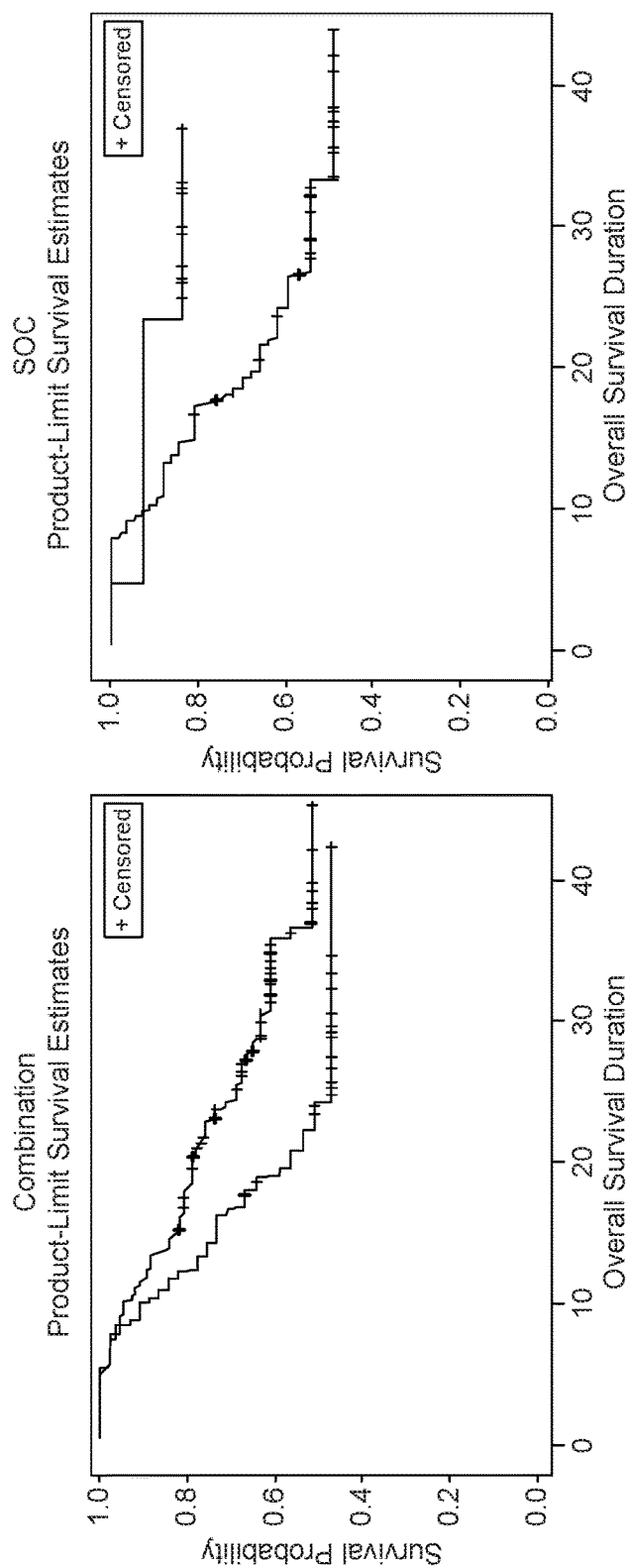

FIG. 8 shows Kaplan-Meier plots of overall survival of patients enrolled in Argos' ADAPT clinical trial divided into groups by baseline % Treg values. Data from patients in the trial's combination treatment arm (AGS-003 with standard of care) is shown in the left panel and data from patients in the Standard of Care arm is shown in the right panel. In the combination treatment arm (left panel), the upper line shows data from patients having baseline % Treg values in the top three quartiles, while the lower line shows data from patients having baseline % Treg values in the bottom quartile. In the Standard of Care arm (right panel), the upper line (as it extends to the right) shows data from patients having baseline % Treg values in the lowest quartile, and the lower line shows data from patients having baseline % Treg values in the top three quartiles.

Figure 9:
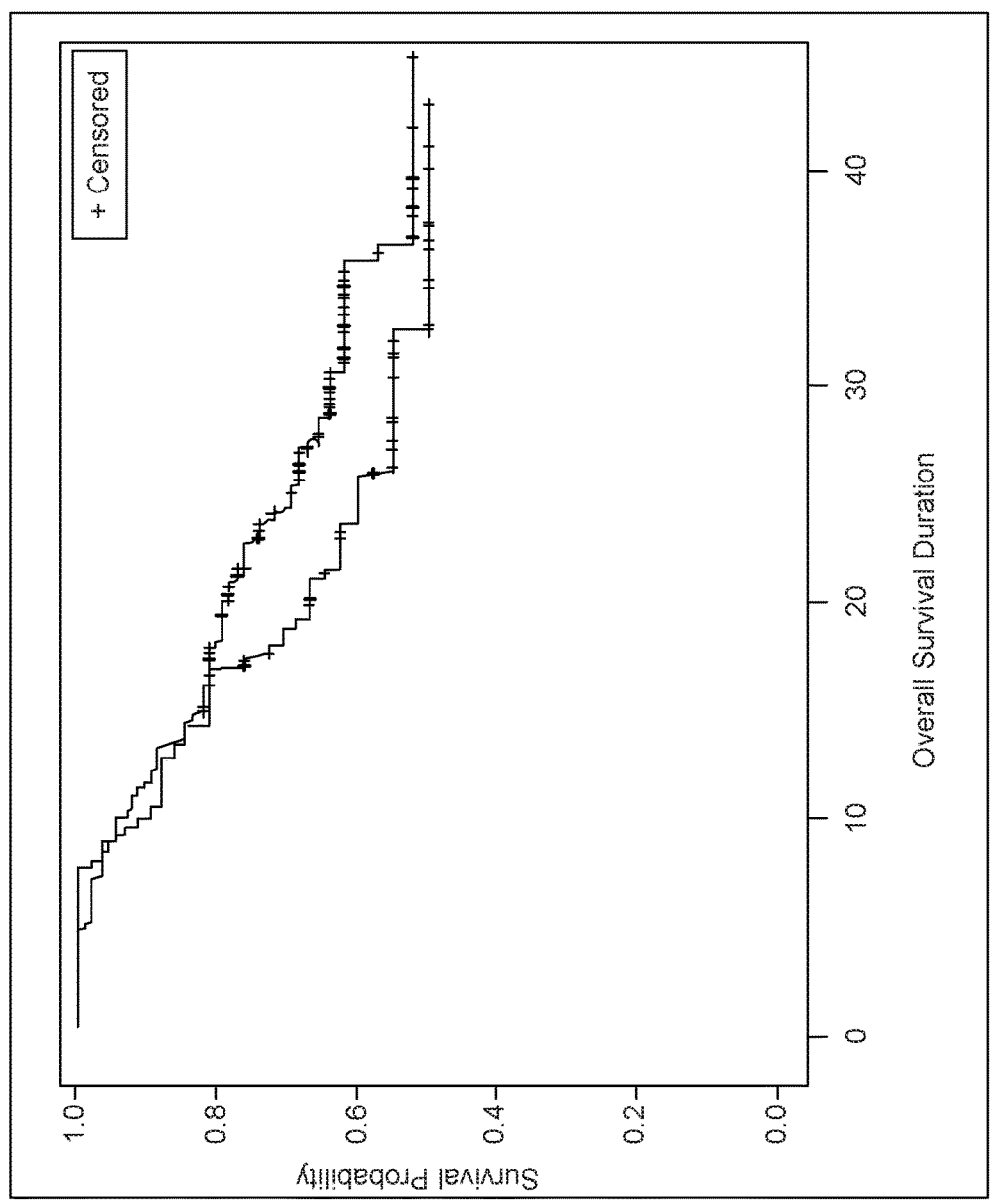

FIG. 9 shows a Kaplan-Meier plot of overall survival of patients enrolled in Argos' clinical trial who had baseline % Treg values in the top 3 quartiles. The hazard ratio of data from patients in the combination treatment arm (AGS-003 with standard of care) to the data from patients in the Standard of Care arm was 0.74.

Figure 10:
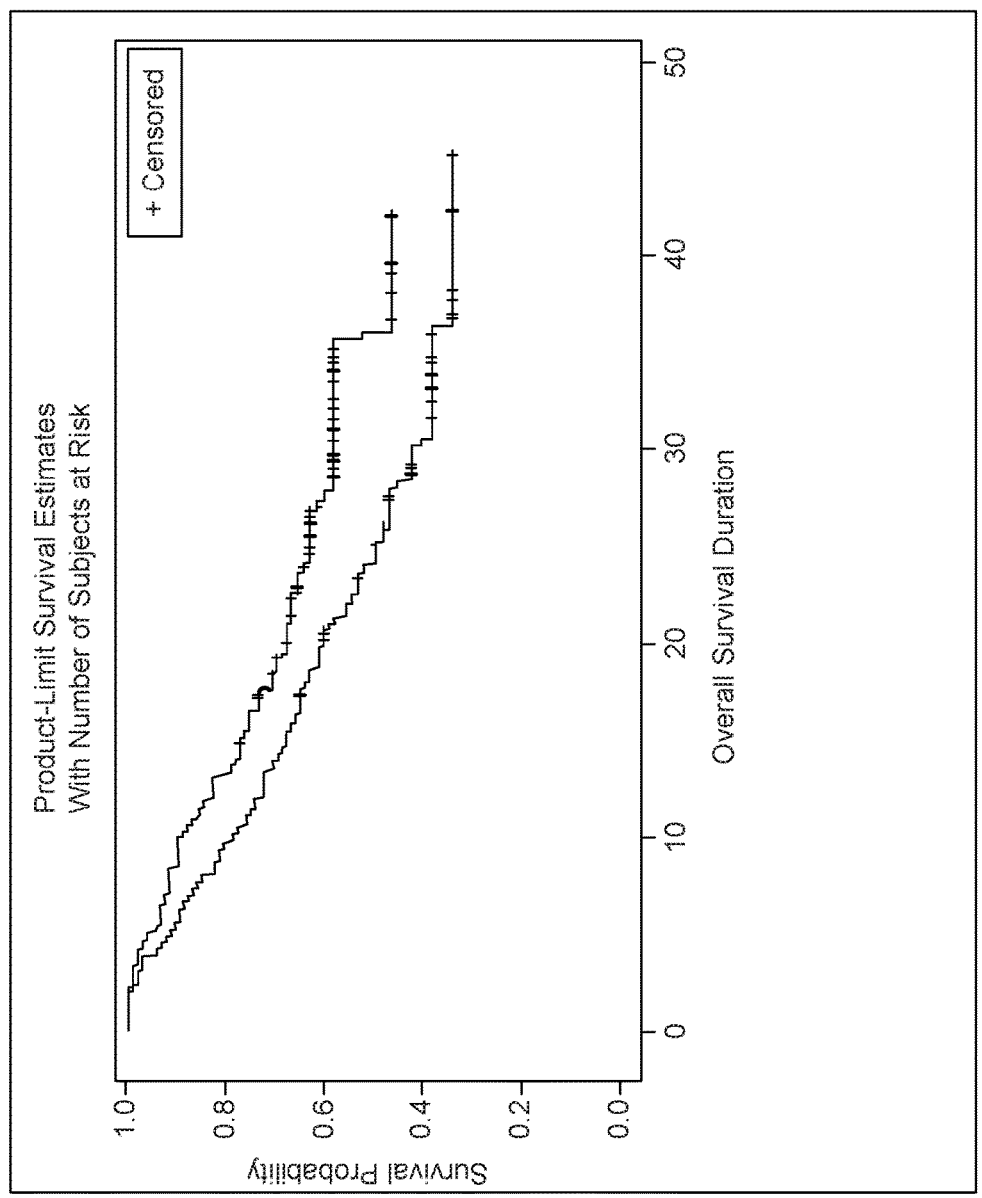

FIG. 10 shows a Kaplan-Meier plot of overall survival of patients enrolled in the combination arm of Argos' clinical trial divided into groups by baseline monocyte counts. The hazard ratio of data from patients with monocyte counts at or below the median (upper line) to the data from patients with monocyte counts above the median (lower line) was 0.6498.

Figure 11:
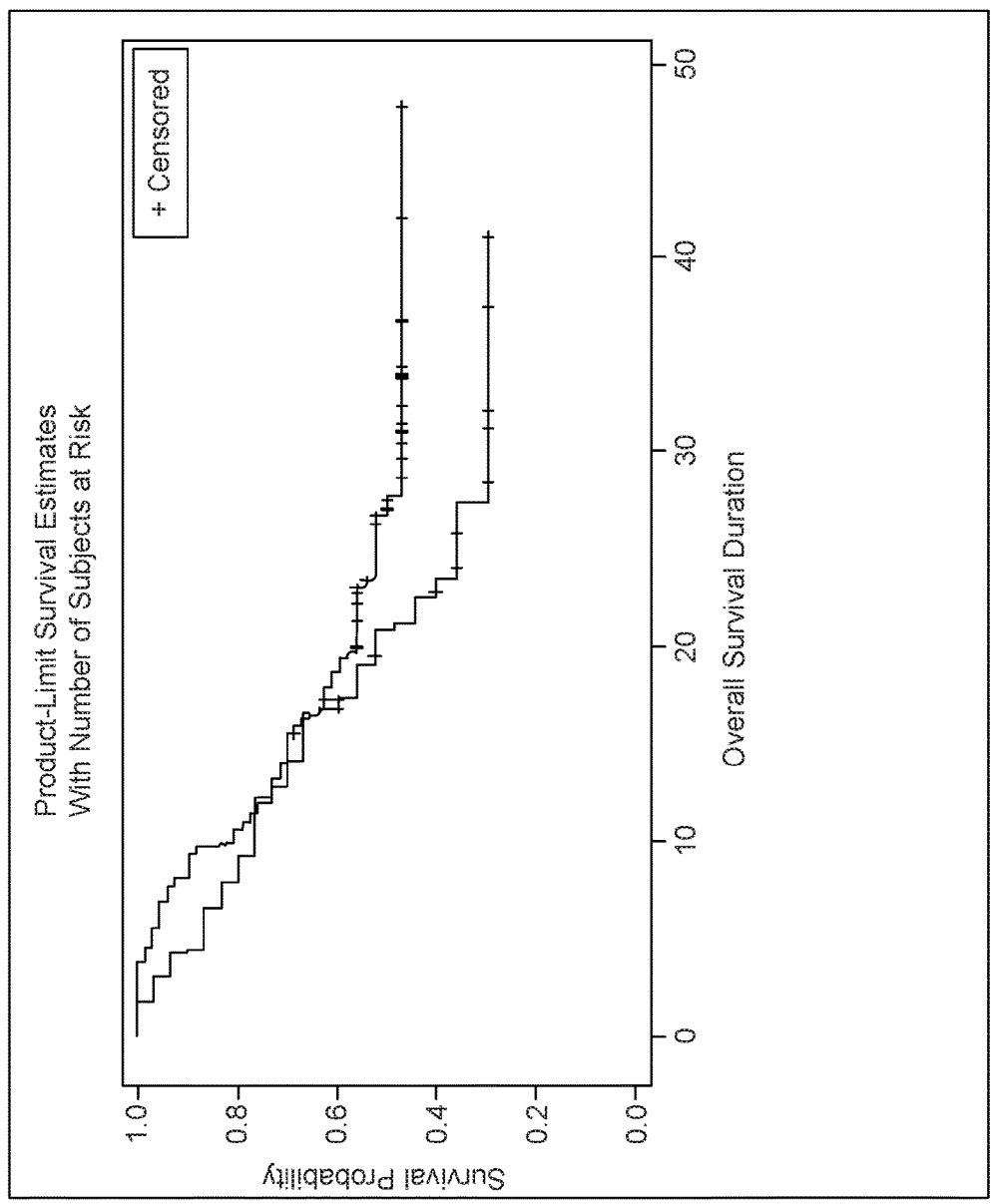

FIG. 11 shows a Kaplan-Meier plot of overall survival of patients enrolled in Argos' clinical trial with the highest quartile of baseline platelet counts. The hazard ratio of data from patients in the combination treatment arm (AGS-003 with standard of care, upper line) to the data from patients in the Standard of Care arm was 0.6954.

DETAILED DESCRIPTION OF THE INVENTION

Surprisingly, the instant inventors have discovered that patients having certain immune system properties are more likely to experience more favorable treatment outcomes from dendritic cell therapy. The invention provides methods of evaluating immune system parameters such as, for example, regulatory T cell ("Treg") counts to identify and treat patients who are likely to experience more favorable treatment outcomes.

Thus, the invention provides methods for treating a human patient with a dendritic cell therapy comprising obtaining at least one value or measurement of the level and/or amount of a particular type of immune cell and/or serum chemistry marker in the patient; confirming that said value or measurement exceeds or is less than the treatment threshold value for that value or measurement, as appropriate; and administering said dendritic cell therapy to said patient. The invention also provides methods for administering a dendritic cell therapy to a patient comprising obtaining at least one value or measurement of the level and/or amount of a particular type of treatment indicator; confirming that said value or measurement exceeds or is less than the treatment threshold value for that value or measurement, as appropriate; and administering said dendritic cell therapy to the patient.

For example, surprisingly, the instant inventors have discovered that patients with high levels of Treg cells are likely to benefit from dendritic cell therapies. Treatment of these patients with an effective dendritic cell therapy produces an immune response, part of which is a decrease in the numbers and/or levels of Treg cells in said patient. In some embodiments, the immune response is measured by evaluating patient DCs in vitro for their ability to produce Treg/eff cells in culture. Thus, it will be understood that the invention also provides methods of stimulating an immune response in a patient comprising obtaining at least one value or measurement of the level and/or amount of a particular type of treatment indicator; confirming that said value or measurement exceeds or is less than the treatment threshold value for that value or measurement, as appropriate; and administering said dendritic cell therapy to the patient, and optionally performing an assay to determine or confirm that the patient's immune response has been stimulated.

By "Tregs" as used herein is intended regulatory T cells. Tregs can be identified by their expression of certain cell surface markers or expression of other genes, such as, for example, CD4+, CD25+, and/or FoxP3+. Tregs can also be distinguished from other types of T cells by their lack of expression of certain genes or markers, such as, for example, CD127. Thus, in some embodiments, the Tregs referred to herein are identified as cells that are CD4+, CD25+, FoxP3+, and CD127−. In addition, Tregs may be identified as one or more of CD3+, PD-1−, and/or CXCR4+. In some embodiments, the Tregs referred to herein are identified by their phenotype as any one, two, three, four, five, or six of, or as all of: CD3+, CD4+, CD25+, FoxP3+, CD127−, PD-1−, and CXCR4+.

Generally as used herein, "+" indicates positive expression, "++" indicates higher expression, "+/−" indicates weaker expression, and "−" indicates very weak or undetectable expression as measured by any suitable method known in the art, such as, for example, by evaluating mean fluorescence intensity (MFI) using flow cytometry. Detailed methods and protocols for measuring expression of cell surface markers and other genes by flow cytometry and comparing expression among different populations and/or subpopulations of cells are known in the art, for example, as discussed in Hasan et al. (2015) Clin. Immunol. 157: 261-76.

In some embodiments, Tregs with suppressor activity are identified by multi-color flow cytometry staining for the combination of positive expression of cell surface phenotype markers CD3, CD4, and CD25 and negative for CD127 expression in conjunction with intracellular expression of the transcription factor FoxP3.

In some embodiments, the invention provides methods using flow-cytometry-based assays to identify cancer patients who are most likely to respond to a therapy (i.e., by induction of an immune response) based on the initial (baseline) numbers or amounts of Tregs in the patient's blood. In some embodiments, the invention provides methods using flow-cytometry-based assays to identify cancer patients for whom a therapy is likely to induce an immune response based on the detection of increases in the number of Tregs in the patient's blood following at least one treatment or dose with that therapy. By "cancer patient" is intended a patient who has been diagnosed with a cancer; in some embodiments, the cancer patients have been diagnosed with metastatic renal cell carcinoma (RCC).

In some embodiments, the invention provides methods of determining whether an immune response was induced in a patient by a treatment, comprising the steps of: quantifying the number of Treg cells present in a sample of a patient's blood to establish a baseline reading; following administration to said patient of a treatment, quantifying the number of Treg cells present in a sample of said patient's blood to establish a post-treatment reading; and comparing said baseline reading and said post-treatment reading to determine whether the frequency or amount of Treg cells present in the sample of the patient's blood has decreased, wherein a significant decrease in the frequency or amount of Treg cells indicates that an immune response was induced in the patient. In some embodiments, said treatment comprises administering to said patient autologous mature DCs prepared in vitro, such as, for example, Rocapuldencel-T (AGS-003).

The working examples herein provide evidence that Foxp3+ Treg effector cells ("Treg/eff cells") proliferate as a result of in vitro culturing with AGS-003 dendritic cells. These Treg/eff cells differ from Tregs by the positive expression of PD-1 and negative expression of the chemokine receptor CXCR4. These Treg/eff cells are a novel population of activated CD4+/FoxP3+/PD-1+/CXCR4− T cells and can be used to measure the immune stimulation resulting from dendritic cell therapy either in vivo or by in vitro culture as demonstrated in the working examples provided.

Thus, in some embodiments, the invention provides methods of determining whether an immune response was induced in a patient by a treatment, comprising the steps of: quantifying the number of Treg/eff cells present in a sample of a patient's blood to establish a baseline reading; following administration to said patient of a treatment, quantifying the number of Treg/eff cells present in a sample of said patient's blood to establish a post-treatment reading; and comparing said baseline reading and said post-treatment reading to determine whether the frequency or amount of Treg/eff cells present in the sample of the patient's blood has increased, wherein a significant increase in the frequency or amount of Treg/eff cells indicates that an immune response was induced in the patient. In some embodiments, the Treg/eff cells are evaluated for proliferation, wherein the presence of a significant or significantly increased population of proliferating Treg/eff cells in the patient following treatment indicates that an immune response was induced in the patient.

In some embodiments, the invention provides methods for treating a human patient with a dendritic cell therapy comprising obtaining at least one value or measurement of a treatment indicator such as, for example, the level and/or amount of a particular type of immune cell and/or serum chemistry marker in the patient's body, body fluids, or tissue; confirming that said value or measurement exceeds or is less than the treatment threshold value for that value or measurement, as appropriate; and administering said dendritic cell vaccine to said patient. In some embodiments, said treatment indicator value or measurement pertains to one or more of: Treg cell count per ml of patient blood or blood component; CD8+CD28+ CTL count; % CD4+CD25+ CD127− FoxP3+ cells among CD4+ cells (or % Treg using other markers or a QAMA assay); blood level of one or more serum chemistry RISK markers, such as, for example, C-reactive protein ("CRP"); and blood level of one or more DC deficiency markers. Serum chemistry RISK markers are known in the art and include, but are not limited to: Alb, CRP, ESR, AST/ALT, Ca, etc.

Thus, in some embodiments the patient will be screened prior to treatment with a dendritic cell therapy for values or counts of treatment indicators such as, for example: level of plasma lymphocytes; CD8+CD28+ cell counts; CD8+CD28+PD-1+ cell counts; counts of CD8+CD28+PD-1+ cells secreting IFN-gamma; percentage of CD4+ cells that are Tregs; blood platelet counts; C-reactive protein (CRP) level; lymphocyte/monocyte ratio; monocyte counts (pre-Elutra); and neutrophil/leukocyte ratio. As used herein, "treatment indicator" refers to a measurement of tumor or patient biology, parameter of blood chemistry, or result of culturing or processing of patient cells that can provide information regarding the likelihood of improvement or successful treatment of a patient who is treated with a dendritic cell therapy. "Treatment threshold value" as used herein refers to the numerical value identified as an upper or lower threshold for a treatment indicator and below which or above which, respectively, treatment of said patient with a dendritic cell therapy is recommended and/or identified as being likely to produce one or more benefits to the patient, i.e., to produce improvement in one or more measurements of patient health or treatment success.

Thus, for example, treatment threshold values prior to treatment of a patient with a dendritic cell vaccine or at a time of initial screening ("baseline") can include, for example, any of: percent of CD4+ cells that are Tregs of at least 1.58%, or at least 1.60%, 1.65%, 1.70%, 1.75%, 1.80%, 1.85%, 1.90%, 2.00%, or a higher percent; absolute number of Tregs per ml of patient blood of at least 500 Tregs/100 microliters of whole blood, or at least 400, 450, 500, 550, 600, 650, 700, 750, 800, 850, 900, 950, or 1000 or more Tregs/100 microliters of whole blood; platelet counts of at least 500,000 or at least 600,000; 650,000; 700,000; 750,000; 800,000; 850,000; 900,000; or 1,000,000 platelets per microliter of blood; C-reactive protein values (hs-CRP) of at least about 4, or 42, or at least 40, 42, 45, 50, 55, 60, 65, 70, or 75 or 76 mg/L; lymphocyte/monocyte ratio of at least 2.50, or at least 2.60, 2.70, 2.75, 2.80, 2.85, 2.90, 3.00, 3.10, 3.20, 3.30, 3.33, or 3.35 or higher; monocyte count (pre-Elutra) of less than 500, 450, 400, 350, 300, 250, 200, or 150 or fewer monocytes/uL of blood; monocytes as a percentage of white blood cells of 7% or less, or less than 6%, 5.5%, 5%, 4.5%, 4%, or 3.5% or less; monocyte/leukocyte ratio of less than 10.0, 9.0, 8.0, 7.0, 6.0, 5.9, 5.5, 5.0, 4.5, 4.0, or 3.0 or less; plasma lymphocyte value corresponding to the median value or above for patients or to the highest quartile of patients; and CD8+CD28+ cell counts or CD8+CD28+PD-1+ cell counts or counts of CD8+CD28+PD-1+ cells secreting IFN-gamma that are equal to or less than the median or that correspond to the lowest quartile of patients.

In some embodiments, treatment threshold values of treatment indicators are determined following processing of the patient's blood for production of a dendritic cell therapy. For example, treatment threshold values include monocytes as a percentage of white blood cells following leukapheresis of less than 26%, or less than 35%, 30%, 28%, 24%, 22%, 20%, 18%, or 15% or less.

In some embodiments, treatment threshold values prior to treatment of a patient with a dendritic cell vaccine or at a time of initial screening ("baseline") can include percent of CD4+ cells that are Tregs of at least 2.5%, or at least 3%, 3.5%, 4%, 4.5%, 5%, 5.5%, 6%, 6.5%, 7%, 8%, or 9% or a higher percent of CD4+ cells that are Tregs. These measurements can be direct cell counts obtained, for example, by flow cytometry, or can be determined using assays known in the art such as, for example, determination of methylation of the FoxP3-TSDR region.

In some embodiments, treatment threshold values include measurements of the dendritic cell therapy produced from the patient's blood. For example, treatment threshold values include viable DCs/dose of at least $1.3 \times 10^7$ viable DCs, or at least $7 \times 10^6$; $9 \times 10^6$, $1 \times 10^7$, $1.5 \times 10^7$, $2 \times 10^7$; $2.5 \times 10^7$; $3 \times 10^7$; or more viable DCs per dose. A "dose" is an aliquot of DCs that is administered or is intended to be administered to a patient. In some embodiments, multiple doses of DCs are produced from a single draw of a patient's blood.

In some embodiments, methods are provided to determine whether treatment of a patient with a dendritic cell vaccine should be continued, or whether alternative treatments should be administered. Data from Argos' ADAPT clinical trial showed that patients in the combination arm who experienced the greatest decrease in % Treg cells from baseline measurement to 48 weeks also showed an increase in overall survival. Accordingly, detecting or monitoring a change in % Tregs of a patient could be informative in deciding whether to continue or discontinue treatment of that patient with doses of dendritic cell vaccines, in deciding whether to administer additional or alternative treatments, or in determining the prognosis for that patient, either by considering the change in % Tregs alone or considering it in combination with other measurements or values.

In some embodiments, treatment of a patient with a dendritic cell therapy or evaluation of a patient will include a step in which more than one treatment threshold value is considered. Thus, for example in some embodiments a method of treatment of a patient will include a step of measuring or determining or considering one or more, two or more, three or more, four or more, five or more, six or more, or seven or more counts or values of treatment indicators selected from the group consisting of: plasma lymphocyte value; CD8+CD28+ cell count; CD8+CD28+PD-1+ cell count; count of CD8+CD28+PD-1+ cells secreting IFN-gamma; percent of CD4+ cells that are Tregs; count of Tregs per unit volume of blood or blood component; platelet count; C-reactive protein (CRP) value; lymphocyte/monocyte ratio; monocyte count (pre-Elutra); and neutrophil/leukocyte ratio, in any combination deemed appropriate and/or considered useful by one of skill in the art. In some embodiments, a method of treatment of a patient comprises obtaining a measurement of C-reactive protein for said patient that is 42 or above and a measurement of % Treg cells (as a percentage of CD4+ cells) that is greater than 1.75% so that the treatment threshold values for CRP and % Treg are met or exceeded.

In some embodiments, the method of treating a patient or the step of considering treatment indicators or threshold values comprises obtaining a prediction of likely treatment success from a multivariable statistical analysis, or a statistical model taking input of two or more treatment indicator values. In some embodiments, a multivariable statistical analysis is used to assess whether a patient is likely to benefit from treatment with a dendritic cell therapy. In some embodiments, the statistical model takes input values for a patient's C-reactive protein level, lymphocyte/monocyte ratio, monocyte/leukocyte ratio, % Tregs, or two or more of these. In some embodiments, the statistical model takes input values for C-reactive protein and percent T-regs. In the methods of the invention, any suitable statistical model may be used with any of the treatment indicators and treatment threshold values that exhibit predictive value for whether a patient will benefit from treatment with a DC therapy;

suitable statistical models, methods, and techniques are well known in the art, and suitable software packages are readily commercially available, for example, from SAS® Institute, Inc., Cary, N.C.

Methods are known in the art for producing mature DCs. Some methods for producing mature DCs are described in detail in: WO2006042177 (Healey et al.); WO2007117682 (Tcherepanova et al.); DeBenedette et al. (2008) *J. Immunol.* 181: 5296-5305; and Calderhead et al. (2008) *J. Immunother.* 31: 731-41. In some of these methods, immature DCs are sequentially signaled with a first signal (an IFN-γ receptor agonist and optionally a TNF-α receptor agonist) to produce CD83$^+$ CCR7$^-$ mature DCs and then are signaled with a second signal (a CD40 agonist) in an amount effective to produce CD83$^+$ CCR7$^+$ mature DCs; various IFN-γ receptor agonists and/or TNF-α receptor agonists may be used. In a method called the "PME-CD40L process" (for Post Maturation Electroporation with CD40L), immature DCs are first phenotypically matured by adding IFN-γ and TNF-α to the culture medium; optionally, PGE$_2$ is also added. Then, approximately 12-30 hours later (in some embodiments about 18 hrs later), the cells are electroporated with CD40L mRNA and, optionally, antigen-encoding mRNA. This PME-CD40L process produces CD83$^+$ CCR7$^+$ mature DCs. Cells harvested from this process after electroporation (e.g., 4 hrs post electroporation) and formulated as a vaccine were shown to mediate maximum immunopotency in in vitro assays.

Dendritic cells made by the PME-CD40L process (herein, "PME-CD40L DCs") differ from previously known dendritic cells because they can support long term antigen-specific CTL effector function and induce a type of effector memory CTLs designated Rapidly Expanding High-Avidity ("REHA") cells (see DeBenedette et al. (2008) *J. Immunol.* 181: 5296-5305). REHA cells retain the capacity to expand, produce cytokines, and kill target cells, and thus provide robust long-term CTL effector function. Thus, PME-CD40L DCs preferentially induce a population of CD28$^+$ CD45RA memory/effector T cells from a population of antigen-specific T cells. PME-CD40L DCs were also shown to produce $T_{SCM}$ cells (WO 2015/127190 (DeBenedette et al.) and corresponding US Pub. No. 20170065690 (DeBenedette et al.)). In some instances, the CD83$^+$ CCR7$^+$ mature DCs transiently express CD40L polypeptide; in some instances, the CD40L is predominantly localized intracellularly rather than on the cell surface.

PME-CD40L DCs exhibit some distinctive characteristics, including: (a) they demonstrate elevated cell surface expression of the co-stimulator molecules CD80, CD83, and CD86; (b) they are CCR7$^+$; and (c) they secrete IL-12 p70 polypeptide or protein, and/or secrete significantly reduced levels (0 to 500 pg per ml per million DCs) of IL-10 (see, e.g., data and experiments presented in WO2006042177 (Healey et al.) and WO2007117682 (Tcherepanova et al.)). These mature CD83$^+$ CCR7$^+$ DCs produce at least 1000 pg IL-12 per 10$^6$ DCs; IL-10 and IL-12 levels can be determined by ELISA of culture supernatants collected at up to 36 hrs post induction of DC maturation from immature DCs (Wierda et al. (2000) *Blood* 96: 2917; Ajdary et al. (2000) *Infection and Immunity* 68: 1760). One of skill in the art can also determine when PME-CD40Ls have been produced by sampling a cell or subpopulation of DCs from a cell population for the presence of mature DCs expressing CD40L mRNA and/or CD40L polypeptide, or expressing interleukin 12 (IL-12) p35 protein. Other characteristics of these cells are discussed, for example, in WO2006042177 (Healey et al.); WO2007117682 (Tcherepanova et al.); DeBenedette et al. ((2008) *J. Immunol.* 181: 5296-5305); and Calderhead et al. ((2008) *J. Immunother.* 31: 731-41).

Immature DCs used to produce PME-CD40L DCs can be isolated or prepared from a suitable tissue source containing DC precursor cells and differentiated in vitro to produce immature DCs. The immature DCs can also be isolated from peripheral blood mononuclear cells (PBMCs) which optionally are treated with an effective amount of granulocyte macrophage colony stimulating factor (GM-CSF) in the presence or absence of interleukin 4 (IL-4) and/or IL-13, so that the PBMCs differentiate into immature DCs. In some embodiments, PBMCs are cultured in the presence of GM-CSF and IL-4 for about 4-7 days, preferably about 5-6 days, to produce immature DCs. In some embodiments, the first signal is given at day 4, 5, 6, or 7, and most preferably at day 5 or 6. In addition, GM-CSF as well as IL-4 and/or IL-13 may be present in the medium at the time of the first and/or second signaling. Alternatively, the immature dendritic cells can be signaled with an effective amount of a TNF-α receptor agonist followed by signaling with a CD40 agonist. The immature DCs may be contacted with PGE$_2$ at about the same time that they receive the first signal of an IFN-γR agonist and a TNF-αR agonist. In some methods, signaling is in the absence of an effective amount of IL-10 and/or IL-6. GM-CSF and at least one of IL-4 or IL-13 may be present in the medium at the time the dendritic cells receive the first and second signals.

Signaling with IFN-γ receptor agonists, TNF-α receptor agonists, and/or CD40 agonists can be accomplished by contacting a cell directly with IFN-γ polypeptides and/or proteins and/or TNF-α polypeptides or proteins and/or CD40 agonists, respectively. Similarly, IFN-γ and TNF-α receptor agonists can be aptamers, antibodies, and the like, that have a similar biological activity to IFN-γ and TNF-α. Alternatively, signaling of a cell with IFN-γR agonists, TNF-αR agonists and/or CD40 agonists can occur upon translation of mRNA encoding such polypeptides or proteins within the dendritic cell. Such mRNA may be introduced into the cell by transfection or other means, and the signaling then occurs upon expression of the IFN-γR agonist, TNF-αR agonist and CD40 agonist polypeptides and/or proteins. Thus, signaling can be initiated by providing the signaling agonist in the culture medium, introduction of the agonist into the cell, and/or upon translation within the dendritic cell of an mRNA encoding an agonistic polypeptide. The methods can be practiced in vivo or ex vivo. Dendritic cells matured ex vivo can then be administered to the subject to induce or enhance an immune response along with the $T_{SCM}$s produced by coculturing with the DCs.

Dendritic cells can be further modified by the administration of an immunogen (e.g., an antigen) to the DCs. The immunogen can be delivered in vivo or ex vivo. The immunogen can be delivered to the cells using methods known in the art, and can be delivered as polypeptides or proteins (e.g., by "pulsing") or as nucleic acids encoding the immunogen (e.g, by transfection or electroporation). In some embodiments, the polynucleotide is an mRNA. In some methods of producing PME-CD40L DCs, the antigen-encoding mRNA is electroporated together with an mRNA encoding a CD40 agonist or substantially concurrent with CD40 agonist signaling.

PME-CD40L DCs can also be transfected with RNA encoding antigens from any pathogen or disease of interest; such antigens can be from one individual subject or multiple subjects and can be from a pathogen infection of the subject from which the antigens are isolated or from another subject. Consensus antigens and pathogen-specific antigens are known in the art and may also be used in methods of preparing PME-CD40L DCs. The DCs will process the antigens and display the antigens on their cell surface; these mature DCs can be used to educate naïve immune effector cells. RNA encoding antigens from a cancer and/or tumor sample removed from a subject may be used to transfect DCs in this manner. RNA encoding HIV antigens from a sample removed from a subject may also be used to transfect DCs. For example, PME-CD40L DCs that were transfected with MART-encoding mRNA stimulated autologous CD8+ T cells to produce responder CD8+ T cells, as described, for example, in WO2006042177 (Healey et al.) and WO2007117682 (Tcherepanova et al.). Also, PME-CD40L matured DCs loaded with total amplified Renal Cell Carcinoma ("RCC") tumor RNA induced a fully autologous CTL response (see WO2006042177 (Healey et al.)).

In some embodiments, PME-CD40L DCs are transfected with RNA encoding part or all of the HIV proteins Gag, Nef, Tat, and Rev, as described in WO2006031870 and U.S. Pub. No. 20080311155 (Nicolette et al.). Briefly, DCs are transfected with RNA encoding one or more polypeptides from multiple strains of HIV present in an individual subject; the RNA is derived from nucleic acid amplification of pathogen polynucleotides. Primers to amplify such pathogen polynucleotides can be designed to compensate for sequence variability between multiple strains of said pathogen, for example, when said pathogen is HIV, as described in WO2006031870 and U.S. Pub. No. 20080311155. Such primers can include, for example, primers disclosed in WO2006031870, including forward and reverse primers for Gag, Nef, Tat, and Rev. The DCs resulting from this process have been shown to be capable of stimulating an immune response to HIV in HIV patients. In this manner, a DC therapy autologous to a patient can be produced and used to stimulate an immune response to the HIV strains found in that patient.

PME-CD40L DCs can also be stored by contacting an enriched dendritic cell population with a suitable cryopreservative under suitable conditions and frozen (see, e.g., WO 2002016560 and U.S. Pat. No. 8,574,901 (Schuler et al.)).

Many methods are known in the art for the isolation and expansion of various cells for in vitro expansion and differentiation into dendritic cells, including $CD34^+$ stem cells (see for example, U.S. Pat. No. 5,199,942). As is apparent to those of skill in the art, dose ranges for differentiating stem cells and monocytes into dendritic cells are approximate. Different suppliers and different lots of cytokine from the same supplier vary in the activity of the cytokine. One of skill can readily titrate each cytokine used to determine the optimal dose for any particular cytokine. Certain cell types can be induced or matured by coculture with other cell types, as is known in the art. The term "coculture" refers to a cell culture known to contain at least two different types of cells.

DCs can be generated from non-proliferating $CD14^+$ precursors (monocytes) in peripheral blood by culture in medium containing GM-CSF and IL-4 or GM-CSF and IL-13 (see, e.g., WO 97/29182; Sallusto and Lanzavecchia (1994) *J. Exp. Med.* 179: 1109 and Romani et al. (1994) *J. Exp. Med.* 180:83). In some embodiments, DCs are autologous to the patient or subject; that is, the DCs or their precursor cells are obtained from the same patient or subject to which they are administered. In other embodiments, the DCs or their precursors are obtained from a different patient to which they are administered (i.e., they are allogeneic or heterologous).

When cells are isolated from an HIV patient, HIV-infected cells may be preferentially removed from the population using reagents such as, for example, CD4-PE40 (e.g., at 25 nM). CD4-PE40 is a recombinant protein consisting of the HIV-1-binding CD4 domain linked to the translocation and ADP-ribosylation domains of *Pseudomonas aeruginosa* exotoxin A; it has been shown to inhibit p24 production in HIV-infected cell cultures and to selectively kill HIV-1-infected cells. To stimulate cell proliferation, OKT3 monoclonal antibody (Ortho Diagnostics™, Inc.) can be added.

Antigens can be prepared from a patient's own cancer cells and loaded into DCs that are then infused back into the patient. For treatment of HIV/AIDS, antigens are prepared from an HIV patient (i.e., a patient infected with HIV) and loaded into DCs that are infused back into the patient. Methods for preparing antigens from HIV patients and preparing DCs that present them are known in the art, for example, as described in WO2006031870 (Nicolette et al.).

Tregs may also produce various cytokines, such as, for example IL-10 and/or TGF-β. Methods are known in the art for detecting and measuring such cytokines. Methods are known in the art to separate cells based on particular functional attributes such as their expression of specific cytokines (e.g., as discussed in Kammula et al. (1999) *J. Immunol.* 12: 6867-75 and Kammula et al. (2008) *J. Transl. Med.* 2008: 60), and cells can be selected on the basis of cytokine expression using a cytokine capture reagent (e.g., as discussed in Brosterhus et al. (1999) *Eur. J Immunol.* 12: 4053-59).

In another aspect, cells can be identified and/or isolated based on their expression of particular genes. Cell surface markers can be particularly useful in this manner. For example, DCs can be distinguished from other cells because they express MHC molecules and costimulatory molecules (e.g., B7-1 and B7-2) and lack markers specific for granulocytes, NK cells, B cells, and T cells. Tregs express CD4, CD25, and FoxP3 but have little or no expression of CD127, which can be used to distinguish them from activated T cells, for example, using flow cytometry. The expression of markers facilitates identification, purification, and separation of these cells from other cells expressing at least one different marker; any suitable combination of markers may be used and is readily determined by one of skill in the art. Negative marker or cell selection may also be used. In this manner, Treg cells and/or Treg/eff cells can be identified, separated, isolated, or enriched from other cells on the basis of expression of one or more of CD4, CD25, FoxP3, CD127, PD-1, and CXCR4. Cells can be isolated and/or characterized by flow cytometry methods such as FACS analysis as well as by any suitable method known in the art. See, e.g., Lowther et al. (2016) *JCI Insight* 1(5): e85935; Raimondi et al. (2006) *J. Immunol.* 176: 2808-16. Thus, for example, Tregs can be identified by multi-color flow cytometry as cells that are positive for (i.e., express at detectable levels) the markers CD4, CD25, and FoxP3, but show low or undetectable levels of expression of CD127. For subsequent use in vivo or in vitro, a specific cell type such as Tregs or Treg/effs can also be enriched, isolated or purified from other cells using magnetic bead isolation of cells having one or more of these markers, or in some instances it may be preferable to remove other cell types from a mixed cell population using appropriate markers. In some embodiments, Tregs can be measured using a QAMA assay ("Quantitative Analysis of Methylated Alleles") as discussed in more detail elsewhere herein.

By "low" or "negative" expression of a cell surface marker or expression of another gene by a cell, group of cells, or cell type is intended that the expression is lower than in another cell, group of cells, or cell type, or that expression is barely detectable or undetectable using methods known in the art (see, e.g., Hasan et al. (2015) *Clin. Immunol.* 157: 261-76).

Labeling agents which can be used to identify, detect, and/or monitor cell antigens (including cell surface markers) are known in the art and include but are not limited to monoclonal antibodies, polyclonal antibodies, proteins, or other polymers such as affinity matrices, carbohydrates or lipids. Detection proceeds by any known method, such as immunoblotting, Western blot analysis, tracking of radioactive or bioluminescent markers, capillary electrophoresis, or other methods which track a molecule based on size, charge or affinity.

Cell separation methods based on the expression of surface markers are known in the art and include the use of magnetic bead isolation, multi-color flow cytometry or FACS sorting (e.g., as discussed in Basu et al. (2010) *J. Vis. Exp.* 41), and microelectromechanical systems chips ("MEMS" chips)-based sorting (e.g., as discussed in Shoji and Kawai (2011) *Top. Curr. Chem.* 2011: 1-25). FACS machines and cell sorters are commercially available (e.g., the BD Bioscience LSRII and the BD FACSAria) and can be used according to manufacturer's instructions.

Cells can be isolated or separated from other cells by positive or by negative selection where appropriate, or by both positive and negative selection. For example, Treg cells can be enriched from a population including other cells such as PBMCs or lymphocytes using negative selection to deplete other cell types followed optionally by positive selection for CD4, CD25, CXCR4 and/or FoxP3. Kits and reagents are known in the art for a variety of purification steps, allowing one of skill in the art to isolate or purify a known cell type; for example, Invitrogen's Dynabeads® Untouched™ Human T cell kit is designed to deplete human B cells, NK cells, monocytes, macrophages, platelets, dendritic cells, granulocytes, and erythrocytes using antibodies including mouse IgG antibodies against non-T cells: human CD14, CD16, CD19, CD36, CD56, CDw123, and CD235a. It will be appreciated from this example that one of skill in the art is capable of selecting particular (often commercially-available) antibodies and selection tools to enrich and/or deplete known cell types from a population of cells.

Selection or detection of cells bearing particular markers can be performed for one marker at a time or for more than one marker at a time (e.g., as discussed in Stemberger et al. (2012) *PLoS One* 4:e35798). Selection or detection can also be performed serially, and different types of selection or detection can be used on a particular group or population of cells in subsequent steps to obtain or detect or monitor a desired subpopulation. Cells can also be selected or identified based on their antigen specificity directly by isolating T cells reactive to HLA-peptide complexes (e.g., as discussed in Keenan et al. (2001) *Br. J. Haematol.* 2: 428-34). Cell markers that are useful for identification, screening, and/or selection include CD4, CD8, CD25, CD27, CD28, CD38, CD57, CD95, CD127, FoxP3, PD-1, HLA-DR, and CD45RA.

The Argos Phase 3 ADAPT clinical trial was designed to evaluate overall survival in subjects with newly diagnosed metastatic Renal Cell Carcinoma ("RCC") patients receiving Rocapuldencel-T (also referred to herein as AGS-003) in combination with standard-of-care treatment ("SOC") versus SOC alone. Patients in the SOC arm were given sunitinib (SUTENT®) or another tyrosine kinase inhibitor ("TKI"), and patients in the AGS-003 arm were given multiple doses of AGS-003 according to the trial protocol in addition to sunitinib or another tyrosine kinase inhibitor ("TKI"). Tyrosine kinase inhibitors suitable for treatment consistent with the standard of care are known in the art, as discussed, for example, in Broekman et al. (2011) *World J. Clin. Oncol.* 2: 80-93. "AGS-003" refers to PME-CD40L DCs containing an RNA antigen payload derived from a patient's own tumor material. The patients' immune response in both arms of the study was evaluated before and after treatment. For SOC patients there was a positive correlation between higher initial Treg cell counts or levels in a patient and a relatively worse treatment progression and/or outcome for that patient. Surprisingly, however, for patients treated with AGS-003 there was a positive association between higher initial Treg counts or levels in a patient and a relatively better treatment progression and/or outcome for that patient, including overall survival. This is surprising because of the finding regarding patients in the SOC arm of the trial and also because of previous reports that patients with high Treg levels typically experience worse treatment progression and/or outcomes (see, e.g., Afzali and Lombardi (2013) *BJU International* 112: 538-9; Schwarzer et al. (2012) *PLOS One* 7:e46600; Griffiths et al. (2007) *Cancer Immunol. Immunother.* 56: 1743-53; Cesana et al. (2006) *J. Clin. Oncol.* 24: 1169-77). In the Argos ADAPT clinical trial, patients in the SOC arm showed a decrease in Treg cells between the first trial visit in which they were treated with sunitinib and the second visit, but patients treated with AGS-003 continued to show a decrease in Tregs in subsequent visits.

In this manner, the invention provides methods for treating a patient comprising the steps of: quantifying the number of Treg cells present in a sample of a patient's blood to establish a baseline reading; evaluating of the Treg count or value to determine whether it exceeds a threshold value; and if so, administering to said patient autologous mature DCs prepared in vitro.

Typical Treg counts or levels in human whole blood range between about 200 and 1000 Tregs/100 microliters of whole blood, with a median at about 500 Tregs/100 microliters of whole blood. Analysis of the clinical trial results showed that the count or level of Tregs for AGS-003 patients with better outcomes in the trial was typically at least 650 Tregs/100 microliters of whole blood prior to beginning treatment with AGS-003. In some embodiments, the cells are measured from whole blood with no purification, culturing or stimulations (e.g., with cytokines or other cells in culture), and the counts or values are the absolute number of Treg cells per 100 microliters of whole blood. Other equivalent measurements in blood fractions or using other units of volume are understood by one of skill in the art to represent the same count, level, or frequency of Tregs in a patient (i.e., in a patient's whole blood). In some embodiments, the ratio of Tregs to other cell types of cells, such as for example T effector cells, may be used; however, this ratio is sometimes affected by the presence of inflammation or disease in a patient.

While Treg cells are sometimes characterized by their expression of CD4, CD25, and FoxP3, it has been reported that activated human non-regulatory T cells transiently express FoxP3 even though they do not have suppressive function. It has also been shown that Tregs differ from these cells in exhibiting demethylation of the region known as FoxP3-TSDR ("Treg Specific Demethylated Region"), and that quantitative PCR assays (QAMA) can be used to assess differences in methylation between Treg cells and other cells and provide a measure of Treg cells in blood samples. Thus, in some embodiments, the count, level, or frequency of Tregs in a patient is assessed indirectly using a quantitative PCR assay to determine methylation of the FoxP3-TSDR region. Such assays are known in the art, as taught, for example, in Tatura et al. (2012) PLoS ONE 7: e49962, "Quantification of Regulatory T Cells in Septic Patients by Real-Time PCR-Based Methylation Assay and Flow Cytometry."

As will be appreciated from this description, the invention also provides a medicament that is a dendritic cell therapy for use in treating a patient having at least one baseline treatment indicator value or count that exceeds or is less than the treatment threshold value for that indicator, as appropriate. In some embodiments, the invention provides a medicament that is a dendritic cell therapy for use in treating a patient having at least two, at least three, or at least four baseline treatment indicator values or counts that exceeds or is less than the treatment threshold value for that indicator, as appropriate. In this manner, for example, the invention provides a medicament that is a dendritic cell therapy for use in treating patients having an initial Treg count or value that exceeds a threshold value that is 1.75% of CD4+ cells are Treg cells or 650 Tregs/100 microliters of whole blood of patient whole blood, or an equivalent measurement per unit volume. In some embodiments the medicament comprises a dendritic cell therapy or a dendritic cell vaccine and a pharmaceutically acceptable carrier. In some embodiments the medicament comprises a dendritic cell therapy or a dendritic cell vaccine and a pharmaceutically acceptable carrier in addition to another pharmaceutical composition, such as, for example, a tyrosine kinase inhibitor. Suitable tyrosine kinase inhibitors for administration to a patient also being treated with dendritic cell vaccines are known in the art, such as, for example, sunitinib or other tyrosine kinase inhibitors such as those discussed, for example, in Broekman et al. (2011) *World J. Clin. Oncol.* 2: 80-93.

By "baseline value" or "baseline" is intended the count or value for a treatment indicator or other measurement for a patient prior to beginning a particular treatment, such as, for example, treatment with sunitinib and/or treatment with AGS-003. By "threshold value" is intended that a patient has an initial Treg count or value of at least about 500 Tregs/100 microliters of whole blood, or at least about 600, 650, 700, 750, 800, 850, 900, or 950 or more Tregs/100 microliters of whole blood.

In some instances, it can be useful to identify proliferating cell populations and/or to determine whether a particular cell type or population is proliferating; suitable methods are known in the art. For example, CFSE can be used in conjunction with other cell markers to identify cell types that are proliferating. The frequency of CFSElo T cells represents the percentage of T cells proliferating in vitro after restimulation, for example with PME-CD40L DCs. Ki67 staining can also be used to monitor cell proliferation using flow cytometry.

The correlation in AGS-003-treated patients between a decrease in Treg cells and favorable response to AGS-003 makes the frequency and/or change in Treg cells in these patients a useful indicator of their immune response. In this manner, the frequency and/or change in Treg cells in a patient following a treatment (for example, with PME-CD40L DCs as in the AGS-003 clinical trial) is a valuable tool for assessing a patient's likely clinical outcome. For example, in some embodiments, treatment with AGS-003 will result in a loss of proliferating (Ki67+) Treg cells that are CD4+/CD25+/FoxP3+/PD-1−, indicating a favorable response. In some embodiments, treatment with AGS-003 will result in a decrease in the frequency and/or number of Tregs per unit volume of blood as determined using assays of methylation of the FoxP3-TSDR region. Similarly, changes in the amount of Treg/eff cells in a patient can be a useful indicator of the patient's immune response, with an increase in the amount of Treg/eff cells and/or the amount of proliferating Treg/eff cells indicating a positive immune response.

By monitoring the frequency and/or change in Treg cells, Treg/eff cells, and/or CTLs in a patient treated with a dendritic cell vaccine or therapy, it is possible to predict or determine whether a treatment of a patient has been or will be effective in inducing an immune response as measured, e.g., by an increase in tumor-specific CTLs and/or progression-free survival. Similarly, by monitoring the frequency and/or change in one or more of Treg cells, Treg/eff cells, and CTLs in a patient, it is also possible to evaluate when a treatment has been effective in inducing an immune response. In some instances, a decrease of at least 20%, 30%, 40%, 50%, 60%, 100%, or 200% or more of Treg cells in a patient will indicate that the patient has had a sufficient immune response that a treatment (e.g., treatment with AGS-003) has reached a treatment threshold and may properly be discontinued. In some instances, an increase of at least 20%, 30%, 40%, 50%, 60%, 100%, or 200% or more of Treg/eff cells and/or CTLs in a patient will indicate that the patient has had a sufficient immune response that a treatment (e.g., treatment with AGS-003) has reached a treatment threshold and may properly be discontinued. Such increases and decreases can be measured directly by cell counts determined using flow cytometry or can be measured indirectly using quantitative PCR assays such as the FoxP3-TSDR QAMA assay (see, e.g., Tatura et al. (2012) PLoS ONE 7: e49962).

Treatment decisions are within the skill of a clinician with the guidance of known measures of patient health and also by measurements of patient cell counts or level as described herein. In this manner, the present invention provides methods of determining whether a treatment might or has been effective and/or whether a particular treatment should be continued or discontinued. In some embodiments, the patient has been diagnosed with cancer such as, for example, metastatic renal cell carcinoma.

In some embodiments, methods of determining or confirming effective treatment of a patient diagnosed with cancer comprise: obtaining an aliquot of blood from the patient; quantifying the number or percentage (for example, relative to other CD4+ cells) of Treg cells, Treg/eff cells, and/or CTLs present in the patient's blood; administering a treatment to said patient comprising DCs; after an interval of time, quantifying the number of the same type of cells present in the patient's blood; and evaluating whether that cell count or value for that patient has increased or decreased. In this manner, a decrease in Treg count, an increase in Treg/eff count, and/or an increase in CTL count can serve as an indicator or measure of a patient's immune response. In some embodiments, the desired result of a treatment is that the immune response has been stimulated so that an decrease in Treg cells can be measured; that is, the Treg count is decreased by at least 10%, 20%, 30%, 40%, 50%, 60%, 70%, 80%, or 90% or more. In these embodiments, a treatment is determined to be effective if it results in such a decrease in Treg count. RECIST criteria can also be used to evaluate patient progress or the effectiveness or progress of treatment, as is well known in the art. In some embodiments, a treatment is determined to be effective if it improves RECIST measurements, increases overall survival of a patient group, or results in progression-free survival for one or more patients.

Also provided by the invention are methods of measuring an immune response in a cancer patient, comprising the steps of: obtaining a sample of the patient's blood for measurements including determining Treg count or value, and/or assessing Treg proliferation; administering autologous mature DCs prepared in vitro to said patient; subsequently obtaining a sample of the patient's blood for determining the quantity, frequency, and/or proliferation of Treg cells post-treatment; and comparing the quantity, frequency, and/or proliferation of Treg cells present in the patient's blood post-treatment to the quantity prior to treatment, wherein a significant decrease of Treg cells and/or a decrease in proliferation indicates that an immune response has been induced in the patient.

Also provided by the invention are methods of measuring an immune response in a cancer patient, comprising the steps of: obtaining a sample of the patient's blood for measurements including determining Treg/eff count or value; administering autologous mature DCs prepared in vitro to said patient; subsequently obtaining a sample of the patient's blood for determining the quantity and/or frequency of Treg/eff cells post-treatment; and comparing the quantity and/or frequency of Treg/eff cells present in the patient's blood post-treatment to the quantity prior to treatment, wherein a significant increase of Treg/eff cells and/or a significant increase in the proportion of Treg/eff cells that are proliferating indicates that an immune response has been induced in the patient. In some embodiments, determining the Treg/eff count or value is performed following culturing a patient's cells (such as, for example, PBMCs) in vitro.

Suitable methods of administering dendritic cell vaccines to a patient are known in the art, and, although more than one route can be used to administer a particular cell composition, a particular route can often provide a more immediate and effective reaction than another route. Administration can be by methods known in the art to successfully deliver a cell into ultimate contact with a subject's blood or tissue cells. Preferred routes of administration include but are not limited to intradermal, intranodal and intravenous administration.

Pharmaceutically acceptable carriers are determined in part by the particular composition being administered and by the particular method used to administer it. Accordingly, there is a wide variety of suitable formulations of pharmaceutical compositions comprising dendritic cells. The dose of cells administered to a subject is in an amount effective to achieve the desired beneficial therapeutic response in the subject over time, such as, for example, to inhibit growth of cancer cells, or to inhibit infection (i.e., an "effective amount"); however, those of skill in the art recognize that a patient can benefit from an increase in any measure of the immune response, even if a complete cure is not achieved.

For administration, dendritic cell vaccines can be administered at a rate determined by the effective dose, the LD-50 of the cell type (or other measure of toxicity), and/or any side-effects of the cell type at various concentrations, as applied to the mass and overall health of the subject. Administration can be accomplished via single or divided doses. The cells of this invention can supplement other treatments for a condition by known conventional therapy, including cytotoxic agents, nucleotide analogues and biologic response modifiers. Similarly, biological response modifiers are optionally added for treatment; for example, the cells are optionally administered with an adjuvant, or cytokines such as GM-CSF, IL-12 or IL-2.

The IFN-γR agonist used in the PME-CD40L process can be IFN-γ or a biologically active fragment thereof, and can be a mammalian IFN-γ or a human IFN-γ. The cDNA and amino acid sequence of human IFN-γ are shown in SEQ ID NOs: 5 and 6 of WO2007117682, respectively. In some embodiments, the IFN-γ has the sequence shown in SEQ ID NO:6 of WO2007117682, or a biologically active fragment thereof. In one embodiment, the IFN-γR comprises a polypeptide having at least 80% sequence identity with SEQ ID NO:6 of WO2007117682. Preferably, the IFN-γR agonist has at least 85%, 90%, 95%, 97%, 98% or 99% sequence identity with SEQ ID NO:6 of WO2007117682. Methods for testing the activity of IFN-γR agonists are known in the art (see, for example, Magro et al. (2004) Br. J. Pharmacol. 142: 1281-92). Immature DCs can be signaled by adding an IFN-γR agonist the culture medium, or by expressing the IFN-γR agonist in the dendritic cell. In some embodiments, the DC is transfected with an mRNA encoding an IFN-γR agonist, such as SEQ ID NO:6 of WO2007117682, or a biologically active fragment thereof. Signaling would then occur upon translation of the mRNA within the dendritic cell. The IFN-γR agonist can be added to the culture medium containing immature DCs. In a preferred embodiment, the culture medium further comprises PGE2 and/or GM-CSF plus IL-4 or IL-13.

The second signal used to produce PME-CD40L DCs is a transient signal with a CD40 agonist, such as, for example, CD40L. The signal can be considered transient if the DCs are loaded with an mRNA encoding a CD40 agonist, or if medium containing a CD40 agonist is removed from the DCs. Thus, persistent expression of a CD40 agonist polypeptide, such as constitutive expression of CD40L from a lentiviral vector, is not considered transient expression. The CD40 agonist signal can also be considered transient if the DCs are loaded/transfected with RNA or with an expression vector encoding a CD40 agonist, provided that either: 1) the promoter driving CD40 agonist expression is not constitutive in DCs, or 2) the expression vector does not integrate into the DC genome or otherwise replicate in DCs.

In some methods of preparing PME-CD40L DCs, the CD40 agonist is a CD40L polypeptide or a CD40 agonistic antibody. In general, ligands that bind CD40 may act as a CD40 agonist, for example, a CD40 agonist can be an aptamer that binds CD40. Preferably, the CD40 agonist is delivered as mRNA encoding CD40L. Administration of the second signal comprising CD40L to the cells by transfection of immature or mature DCs with CD40L mRNA produces the modified PME-CD40L DCs that induce immunostimulatory responses rather than immunosuppressive ones.

In some methods used to produce PME-CD40L DCs, CD40L-mRNA-transfected dendritic cells are cultured in medium containing IFN-γ (and optionally $PGE_2$) immediately after transfection and thus prior to translation of the CD40L mRNA to produce an effective amount of a CD40L signal. In this situation, although IFN-γ is added after transfection with CD40L mRNA, the dendritic cells receive the IFN-γ signal prior to the signal that results from the translation of the CD40L mRNA. Thus, the order in which the agents are delivered to the cells is important only in that CD40L signaling must occur after IFN-γ signaling. In these methods, the signaling of the DCs can occur in vivo or ex vivo, or alternatively one or more signaling step may occur ex vivo and the remaining steps of the method can occur in vivo.

As used herein, "CD40 Ligand" (CD40L) encompasses any polypeptide or protein that specifically recognizes and activates the CD40 receptor and activates its biological activity. The term includes transmembrane and soluble forms of CD40L. In preferred embodiments, the CD40 agonist is a mammalian CD40L, preferably a human CD40L. A human CD40L cDNA and the corresponding amino acid sequence are shown in SEQ ID NOs:1 and 2 of WO2007117682, respectively.

In some methods used to prepare PME-CD40L DCs, the method comprises the sequential steps of: (a) signaling isolated immature dendritic cells (iDCs) with a first signal comprising an interferon gamma receptor (IFN-γR) agonist and a TNF-αR agonist, to produce IFN-γR-agonist-signaled dendritic cells; and (b) signaling said IFN-γR-agonist-signaled dendritic cells with a second transient signal comprising an effective amount of a CD40L polypeptide to produce CD83+ CCR7+ mature dendritic cells, wherein the CD40L polypeptide consists essentially of amino acid residues 21-261 of SEQ ID NO:2 of WO2007117682 or a polypeptide having at least 80% sequence identity to amino acid residues 21-261 of SEQ ID NO:2 of WO2007117682.

In some methods used to prepare PME-CD40L DCs, the method comprises the sequential steps of: (a) culturing isolated immature dendritic cells (iDCs) with an interferon gamma receptor (IFN-γR) agonist in the presence of a TNF-αR agonist and PGE2 for approximately 12 to 30 hours to produce CD83+ mature dendritic cells; and (b) approximately 12 to 30 hours after initiating step (a), transfecting said CD83+ mature dendritic cells (mDCs) with mRNA encoding a CD40L polypeptide consisting of amino acid residues 21-261 of SEQ ID NO:2 of WO2007117682 and an mRNA encoding one or more antigens to produce CD83+ CCR7+ mature dendritic cells.

The method used to produce PME-CD40L DCs can also include delivering to the immature or mature DCs an effective amount of an antigen which will be then be processed and presented by the mature DCs. Antigens can be naturally occurring or recombinantly produced. The antigens can be delivered to the cells as polypeptides or proteins or as nucleic acids encoding them using methods known in the art. In some methods, one or more polynucleotides encoding one or more antigens are introduced into the iDCs, signaled DCs or CCR7+ mature DCs by methods known to those of skill in the art such as electroporation. Most preferably, the polynucleotide is an mRNA. In preferred embodiments, the antigen or antigen-encoding mRNA is introduced together with an mRNA encoding a CD40 agonist or substantially concurrent with CD40 agonist signaling.

Methods of loading dendritic cells with antigens are known to those of skill in the art. In one embodiment, the dendritic cells are cultured in medium containing the antigen. The DCs then take up and process the antigen on the cell surface in association with MEW molecules. Preferably, the DCs are loaded with antigen by transfection with a nucleic acid encoding the antigen, for example, an mRNA. An mRNA encoding the antigen can be introduced into the DC, and may be cotransfected with an mRNA encoding a CD40L polypeptide. Methods of transfecting DCs are known to those of skill in the art.

An antigen can be a single known antigen or can be a collection of antigens. A collection of antigens may come from one particular source, such as for example a patient's cancer cells or HIV-infected cells, or may come from several sources, such as for example HIV-infected cells from several different patients. Antigens for use in methods of producing PME-CD40L DCs include, but are not limited to, antigens from: pathogens, pathogen lysates, pathogen extracts, pathogen polypeptides, viral particles, bacteria, proteins, polypeptides, cancer cells, cancer cell lysates, cancer cell extracts, and cancer-cell-specific polypeptides. For example, antigens that can be used to produce PME-CD40L DCs include well-known antigens such as, for example, MART-1.

The antigen can alternatively have a structure that is distinct from any naturally-occurring compound, or can be a fusion protein produced by linking a portion of sequence from a first polypeptide (e.g., a first antigen) to a portion of sequence from a second polypeptide (e.g., a second antigen, a signal sequence, a transmembrane domain, a purification moiety, etc.) by means of a peptide bond. Those of ordinary skill in the art will appreciate the diversity of such fusion proteins for use in accordance with the present invention.

In preferred embodiments, the antigen provided to the dendritic cells is from cancer cells or a pathogen. The cancer cells can be any type of cancer cells, including renal cancer cells (e.g., from renal cell carcinoma), multiple myeloma cells or melanoma cells. Preferred pathogens include HIV and HCV. In preferred embodiments, the antigen is delivered to the DCs in the form of RNA isolated or derived from cancer cells or a pathogen or pathogen-infected cells (e.g., HIV-infected cells). Methods for RT-PCR of RNA extracted from any cells (e.g., cancer cells or pathogen-infected cells), and in vitro transcription are disclosed in WO2006031870 (Nicolette et al.) and U.S. Pub. 20070248578 (Tcherepanova et al.), the contents of which are incorporated by reference.

As used in the specification and claims, the singular form "a," "an" and "the" include plural references unless the context clearly dictates otherwise. For example, the term "a cell" includes a plurality of cells, including mixtures thereof.

As used herein, the term "comprising" is intended to mean that the compositions and methods include the recited elements, but does not exclude others. "Consisting essentially of," when used to define compositions and methods, shall mean excluding other elements of any essential significance to the combination. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps. Embodiments defined by each of these transition terms are within the scope of this invention.

The term "antigen" is well understood in the art and includes any substance which is immunogenic, i.e., an immunogen. The term "antigen" or "immunogen" applies to collections of more than one immunogen, so that immune responses to multiple immunogens may be modulated simultaneously. Moreover, the term includes any of a variety of different formulations of immunogen or antigen. The term "tumor associated antigen," "tumor antigen," or "TAA" refers to an antigen that is associated with a tumor. Examples of well-known TAAs include gp100, MART and MAGE. Other tumor antigens may be specific to a particular tumor in a particular patient.

The term "major histocompatibility complex" or "MHC" refers to a complex of genes encoding cell-surface molecules that are required for antigen presentation to T cells and for rapid graft rejection. In humans, the MEW is also known as the "human leukocyte antigen" or "HLA" complex. The proteins encoded by the MEW are known as "MEW molecules" and are classified into Class I and Class II MHC molecules, as is well known in the art.

The term "antigen presenting cells (APCs)" refers to a class of cells capable of presenting one or more antigens in the form of peptide-MHC complex recognizable by specific effector cells of the immune system, and thereby inducing an effective cellular immune response against the antigen or antigens being presented. APCs can be intact whole cells such as macrophages, B-cells, endothelial cells, activated T-cells, and dendritic cells. While many types of cells may be capable of presenting antigens on their cell surface for T-cell recognition, only dendritic cells have the capacity to present antigens so as to activate naive T-cells for cytotoxic T-lymphocyte (CTL) responses.

The term "dendritic cells" (herein also, "DCs") refers to a diverse population of morphologically similar cell types found in a variety of lymphoid and non-lymphoid tissues (see, e.g., Steinman (1991) *Ann. Rev. Immunol.* 9: 271-296). Dendritic cells constitute the most potent and preferred APCs in the organism. DCs can be differentiated from monocytes but are phenotypically distinct from monocytes; for example, CD14 antigen is not found in dendritic cells but is expressed by monocytes. Also, mature dendritic cells are not phagocytic, whereas monocytes are strongly phagocytosing cells. It has been shown that mature DCs can provide all the signals necessary for T cell activation and proliferation.

The term "immune effector cells" refers to cells capable of binding an antigen and which mediate an immune response. These cells include, but are not limited to, T cells, B cells, monocytes, macrophages, NK cells and cytotoxic T lymphocytes (CTLs). A "naïve" immune effector cell is an immune effector cell that has never been exposed to an antigen capable of activating that cell. Activation of naive immune effector cells requires both recognition of the peptide:MHC complex and the simultaneous delivery of a costimulatory signal by a professional APC for the cells to proliferate and differentiate into antigen-specific armed effector T cells.

As used herein, the term "educated, antigen-specific immune effector cell" is an immune effector cell as defined above which has previously encountered an antigen. In contrast to its naïve counterpart, activation of an educated, antigen-specific immune effector cell does not require a costimulatory signal; recognition of the peptide:MHC complex is sufficient.

"Activated," when used in reference to a T cell, implies that the cell is no longer in $G_0$ phase, and begins to produce one or more of cytotoxins, cytokines and other related membrane-associated proteins characteristic of the cell type (e.g., $CD8^+$ or $CD4^+$), and is capable of recognizing and binding any target cell that displays the particular peptide/MHC complex on its surface, and releasing its effector molecules.

"Immune response" broadly refers to the antigen-specific responses of lymphocytes to foreign substances. Any substance that can elicit an immune response is said to be "immunogenic" and is referred to as an "immunogen". An immune response can be humoral (via antibody activity) or cell-mediated (via T cell activation). As used herein, the phrase "inducing an immune response in a subject" or to induce an immune response in a subject is understood in the art and refers to an increase of at least about 2-fold, or alternatively at least about 5-fold, or alternatively at least about 10-fold, or alternatively at least about 100-fold, or alternatively at least about 500-fold, or alternatively at least about 1000-fold or more in an immune response to an antigen which can be detected or measured, after introducing the antigen into the subject, relative to the immune response (if any) before introduction of the antigen into the subject. In some embodiments, a treatment is considered to have induced an immune response to an antigen in a subject if an immune response is increased by at least 20%, 30%, 40%, 50%, 60%, 70%, 80%, 90%, 100%, or more in comparison to the immune response exhibited by the subject to the antigen before the treatment. An immune response to an antigen includes but is not limited to: the production of an antigen-specific antibody or an increase in the production of antigen-specific antibodies; an increase or decrease in the amount or frequency of an identifiable immune cell type; and the production of an immune cell expressing on its surface a molecule which specifically binds to an antigen. Methods of determining whether an immune response to a given antigen has been induced are well known in the art. For example, antigen-specific antibody can be detected using any of a variety of immunoassays known in the art, including, but not limited to, an ELISA assay.

As used herein, the term "cytokine" refers to any one of the numerous factors that exert a variety of effects on cells, for example, inducing growth or proliferation. Non-limiting examples of cytokines which may be used alone or in combination in the practice of the present invention include interleukin-2 (IL-2), interleukin-12 (IL-12), and granulocyte macrophage-colony stimulating factor (GM-CSF). Cytokines are readily commercially available, and may be 'natural' purified cytokines or may be recombinantly produced.

The terms "polynucleotide," "nucleic acid," and "nucleic acid molecule" are used interchangeably to refer to polymeric forms of nucleotides of any length. The polynucleotides may contain deoxyribonucleotides, ribonucleotides, and/or their analogs. The term "polynucleotide" includes, for example, a gene or gene fragment, plasmids, vectors, isolated DNA of any sequence, isolated RNA of any sequence, nucleic acid probes, and primers. As used herein, mRNA refers to an RNA that can be translated in a dendritic cell. Such mRNAs typically are capped and have a ribosome binding site (Kozak sequence) and a translational initiation codon. As used herein, an RNA corresponding to a cDNA sequence refers to an RNA sequence having the same sequence as the cDNA sequence, except that the nucleotides are ribonucleotides instead of deoxyribonucleotides, and any thymine (T) bases in DNA are replaced by uracil (U) bases in the RNA.

The term "peptide" is used in its broadest sense to refer to a compound of two or more subunit amino acids, amino acid analogs, or peptidomimetics. The subunits may be linked by peptide bonds or, in some embodiments, by other bonds, e.g., ester, ether, etc. As used herein the term "amino acid" refers to either natural and/or unnatural or synthetic amino acids, including glycine and both the D and L optical isomers, amino acid analogs and peptidomimetics. A peptide of three or more amino acids is commonly called an oligopeptide if the peptide chain is relatively short, whereas if the peptide chain is long, the peptide is commonly called a polypeptide or a protein.

A "conservative alteration" to a polypeptide or protein is one that results in an alternative amino acid of similar charge density, hydrophilicity or hydrophobicity, size, and/or configuration (e.g., Val for Ile). In comparison, a "nonconservative alteration" is one that results in an alternative amino acid of differing charge density, hydrophilicity or hydrophobicity, size and/or configuration (e.g., Val for Phe). The means of making such modifications are well-known in the art.

The term "genetically modified" means containing and/or expressing a foreign gene or nucleic acid sequence which in turn modifies the genotype or phenotype of the cell or its progeny. In other words, it refers to any addition, deletion or disruption of a cell's endogenous nucleotides.

As used herein, "expression" of polynucleotides refers to the processes by which polynucleotides are transcribed into mRNA and mRNA is translated into peptides, polypeptides, or proteins. If the polynucleotide is derived from genomic DNA of an appropriate eukaryotic host, expression may include splicing of the mRNA. Regulatory elements required for expression are known in the art and include promoter sequences to bind RNA polymerase and transcription initiation sequences for ribosome binding. Appropriate vectors for bacterial and/or eukaryotic expression are known in the art and are available commercially.

"Under transcriptional control" is a term understood in the art and indicates that transcription of a polynucleotide sequence (usually a DNA sequence) depends on its being operatively linked to an element which contributes to the initiation of, or promotes, transcription. "Operatively linked" refers to a juxtaposition wherein the elements are in an arrangement allowing them to function.

A "gene delivery vehicle" is defined as any molecule that can carry inserted polynucleotides into a host cell. Examples of gene delivery vehicles include liposomes, biocompatible polymers, and other recombination vehicles used in the art which have been described for expression in a variety of eukaryotic and prokaryotic hosts. "Gene delivery," "gene transfer," "transfection" and the like as used herein, refer to the introduction of an exogenous polynucleotide into a host cell regardless of the method used for the introduction. Transfection refers to delivery of any nucleic acid to the interior of a cell and may include a variety of techniques such as: electroporation; protein-based, lipid-based and cat-ionic-ion-based nucleic acid delivery complexes; viral vectors; "gene gun" delivery; and various other techniques known in the art. The introduced polynucleotide can be stably maintained in the host cell or may be transiently expressed. In preferred embodiments, an mRNA is introduced into a DC and is transiently expressed. Stable maintenance typically requires that the introduced polynucleotide either contains an origin of replication compatible with the host cell or integrates into a replicon of the host cell such as an extrachromosomal replicon (e.g., a plasmid) or a nuclear or mitochondrial chromosome. A number of vectors are capable of mediating transfer of genes to mammalian cells and are known in the art.

The sequence of a polynucleotide or portion thereof (or a polypeptide or portion thereof) has a certain percentage of "sequence identity" to another sequence (for example, 80%, 85%, 90%, or 95%) when that percentage of bases or amino acids are the same when the two sequences are aligned and compared. The proper alignment and the percent sequence identity between two sequences can be determined using one of the well-known and publicly available alignment programs with default parameters, such as, for example, "BLAST."

The term "isolated" means separated from constituents, cellular and otherwise, with which the polynucleotide, peptide, polypeptide, protein, antibody, or fragments thereof, are normally associated in nature. For example, an isolated polynucleotide is one that is separated from the 5' and 3' sequences with which it is normally associated in the chromosome. A mammalian cell such as a dendritic cell is isolated from an organism if it is removed from the anatomical site from which it is found in an organism. In addition, a "concentrated," "separated," or "diluted" polynucleotide, peptide, polypeptide, protein, antibody, or fragment(s) thereof, is distinguishable from its naturally occurring counterpart in that the concentration or number of molecules per volume is greater than that of its naturally occurring counterpart.

"Host cell," "target cell," or "recipient cell" are intended to include any individual cell or cell culture which can be or have been recipients for vectors or the incorporation of exogenous nucleic acid molecules, polynucleotides and/or proteins. It also is intended to include progeny of a single cell. In some instances, a progeny cell may not be completely identical (in morphology or in genomic or total DNA complement) to the original parent cell due to natural, accidental, or deliberate mutation. The cells may be prokaryotic or eukaryotic, and include but are not limited to bacterial cells, yeast cells, animal cells, and mammalian cells, e.g., murine, rat, simian or human.

A "subject" or "patient" is a mammal; in many embodiments, a patient is a human patient. A subject or patient can also be any other mammal, including a monkey or ape, or any domestic animal such as a dog, cat, horse, etc.

By "cancer" is meant the abnormal presence of cells which exhibit relatively autonomous growth, so that a cancer cell exhibits an aberrant growth phenotype characterized by a significant loss of cell proliferation control (i.e., it is neoplastic). Cancerous cells can be benign or malignant. In various embodiments, cancer affects cells of the bladder, blood, brain, breast, colon, digestive tract, lung, ovaries, pancreas, prostate gland, or skin. The definition of a cancer cell, as used herein, includes not only a primary cancer cell, but also any cell derived from a cancer cell ancestor, including metastasized cancer cells, in vitro cultures, and cell lines derived from cancer cells. Cancer includes, but is not limited to, solid tumors, liquid tumors, hematologic malignancies, renal cell carcinoma, melanoma, breast cancer, prostate cancer, testicular cancer, bladder cancer, ovarian cancer, cervical cancer, stomach cancer, esophageal cancer, pancreatic cancer, lung cancer, neuroblastoma, glioblastoma, retinoblastoma, leukemias, myelomas, lymphomas, hepatoma, adenomas, sarcomas, carcinomas, blastomas, etc. When referring to a type of cancer that normally manifests as a solid tumor, a "clinically detectable" tumor is one that is detectable on the basis of tumor mass, e.g., by such procedures as CAT scan, magnetic resonance imaging (MM), X-ray, ultrasound or palpation. Biochemical or immunologic findings alone may be insufficient to meet this definition.

The term "culturing" refers to the in vitro maintenance, differentiation, and/or propagation of cells in suitable media.

By "enriched" is meant a composition comprising cells present in a greater percentage of total cells than is found in another composition, such as, for example, the tissues where they are present in an organism or a group, mixture, or culture of cells in which they were previously present. Cells that are 'enriched' in a composition (e.g., an aliquot of media or storage buffer) are present as more than 10%, 20%, 30%, 40%, 50%, 60%, or 70% of the cells in that composition. Similarly, cells are considered to be "purified" or "isolated" if cells of a particular cell type (e.g., Treg cells) are present as more than 30%, 40%, 50%, 60%, 70%, 80%, 90%, or 95% or 99% of the cells in a composition (e.g., an aliquot of media or storage buffer). Conversely, by "depleted" is intended that the frequency of that cell type is decreased in a particular composition or group of cells, e.g., by at least 10%, 20%, 30%, 40%, 50%, 60%, 70%, 80%, or 90% or more, or 100%. By "enriching" or "enrichment" as used herein is intended that cells are "enriched" using positive selection to selectively or preferentially remove them from a population or group of cells, or that cells are "enriched" using negative selection to selectively or preferentially remove other cells from a starting population or group of cells so that the desired cell type(s) remain. Positive and/or negative selection can be readily accomplished using materials and techniques known in the art. For example, cells expressing a particular cell surface marker can be separated from other cells using monoclonal antibodies that bind to the marker and are coupled to columns or magnetic beads; the separation is readily performed according to standard techniques and/or manufacturer or provider directions.

By "cell surface marker" (sometimes herein referred to as "marker" or "cell marker") is intended a molecule expressed on the surface of a cell that can be detected using any suitable method, for example, using labeled antibodies or other means known in the art. A cell surface marker can comprise a protein, glycoprotein, or group of proteins and/or glycoproteins. In some instances a cell surface marker is known to correlate with or be indicative of a particular cell type or one or more cell functions. Certain cell populations can be identified by expression of a particular set or combination of markers, or some subset thereof.

By "positive expression" or "positive for" with reference to a cell surface marker or other marker as used herein is generally intended that the marker is expressed at detectable levels on a cell or in a group of cells or population of cells. In some instances, "positive expression" or "positive for" is used to refer to cells that express a particular cell surface marker at levels significantly above background levels or "low" or "negative" levels, which can be evaluated by comparison to other cells or other groups or populations of cells, or can be a selected level of expression identified as background, low, or negative. One of skill in the art is familiar with techniques for detecting expression of a marker and for determining the level or levels of expression that distinguish "positive" expression from "background" or "negative" expression. Cells that have "positive expression" or are "positive for" a particular marker can exhibit expression that is at least 10%, 20%, 30%, 40%, 50%, 60%, 70%, 100%, 150%, 200%, 300%, 400%, or 500% higher than background expression, or at least 10-fold, 20-fold, 30-fold, 40-fold, 50-fold, 60-fold, or 100-fold or higher than background, low, or negative expression. In some embodiments, the marker is expressed intracellularly but the expression is detectable using techniques known in the art. Generally, expression of a marker is detected with moieties that bind the marker (e.g., antibodies) that are coupled to a fluorescent label or other label that can be measured using a FACS device according to the manufacturers or provider's directions, for example, as demonstrated by the experiments described in the working examples herein and known in the art (see, e.g., Hasan et al. (2015) *Clin. Immunol.* 157: 261-76).

A "pharmaceutical composition" is intended to include the combination of an active agent with a carrier, inert or active, making the composition suitable for diagnostic or therapeutic use in vitro or in vivo. The term "pharmaceutically acceptable carrier" encompasses any of the standard pharmaceutical carriers, such as a phosphate buffered saline solution, water, and emulsions, such as an oil/water or water/oil emulsion, and various types of wetting agents. The compositions also can include stabilizers and preservatives. For examples of carriers, stabilizers and adjuvants, see Martin, *Remington's Pharmaceutical Sciences,* 18th Ed. (Mack Publ. Co., Easton (1990)).

An "effective amount" is an amount sufficient to produce any beneficial or desired results, such as enhanced immune response, treatment, prevention or amelioration of a medical condition (disease, infection, etc). An effective amount can be administered in one or more administrations, applications or dosages. Suitable dosages will vary depending on body weight, age, health, disease or condition to be treated and route of administration; methods of determining an effective amount are known in the art. It is understood by those of skill in the art that any positive immune response can provide a benefit to a patient (e.g., a cancer patient), even if the patient is not completely cured of the cancer, for example, by strengthening the patient's immune response so that other treatments may be more effective than they would have been otherwise.

As used herein, "signaling" means contacting an immature or mature dendritic cell with an IFN-γ receptor agonist, a TNF-α receptor agonist, a CD40L polypeptide or other CD40 agonist. In one embodiment, such agonists are provided externally, (e.g., in the cell culture medium). In another embodiment, the polypeptide agonist is provided via transfection of an immature or mature dendritic cell with a nucleic acid encoding the polypeptide. In cases where the polypeptide(s) is provided by transfecting a dendritic cell with a nucleic acid encoding the polypeptide, signaling is effected upon translation of an mRNA encoding the polypeptide, rather than upon transfection with the nucleic acid. As used herein, the term "mature dendritic cells" means dendritic cells that demonstrate elevated cell surface expression of co-stimulator molecule CD83, compared to immature DCs (iDCs).

As used herein, by the term "significant difference" is intended that an increase or decrease in a measured parameter is statistically significant as determined using an appropriate statistical test. Such methods are known in the art and a proper test is readily selected by one of skill in the art.

Throughout this disclosure, various publications, patents and published patent specifications are referenced by an identifying citation. The disclosures of these publications, patents and published patent specifications are hereby specifically incorporated by reference into the present disclosure to more fully describe the state of the art to which this invention pertains.

The practice of the present invention employs, unless otherwise indicated, conventional techniques of molecular biology (including recombinant techniques), microbiology, cell biology, biochemistry and immunology, which can readily be performed by one of skill in the art. Such techniques are known in the art and explained in the literature. In accordance with the above description, the following examples are intended to illustrate, but not limit, the various aspects of this invention.

EXPERIMENTAL EXAMPLES

Example 1

DC Maturation Process and Evaluation

PME-CD40L dendritic cells (DCs) were prepared essentially as described in Amin et al. (2015) *J. Immunother. Cancer* 3:14 (referred to herein as "AGS-003" or "AGS-003 DCs"). Briefly, autologous tumor total RNA was isolated from nephrectomy or metastasectomy tissue samples and messenger RNA was amplified using RT/PCR and in vitro transcription technologies as previously described in Slagter-Jager et al. (2013) *Mol. Ther. Nucl. Acids* 2013: 2e91. CD40L RNA was manufactured using in vitro transcription and a post-transcriptional capping method as described in Tcherepanova et al. (2008) *PLoS One* 3(1): e1489. Patients had leukapheresis at a clinical site's donor center using a COBE Spectra® Leukapheresis System (Gambro BCT, Lakewood, Colo.). Monocytes were cultured in AIM-V media with GM-CSF (Berlex) and IL-4 (R&D Systems) to generate immature DCs that were then matured using TNF-alpha (R&D Systems), IFN-gamma (InterMune), and prostaglandin E2 (Sigma). Mature DCs were electroporated with the amplified tumor RNA and CD40L RNA using a post-maturation electroporation protocol (Calderhead et al. (2008) *J. Immunother.* 31:731-41).

The final AGS-003 product was formulated as $1.4 \times 10^7$ DC/0.7 mL in 80% autologous plasma, 10% dextrose (50% w/v) (Hospira), and 10% DMSO (Sigma) and cryopreserved in liquid nitrogen vapor phase. Thawed samples of final product were assessed for sterility, mycoplasma, endotoxin, and viability prior to release for clinical use.

For flow cytometric analysis, DCs were harvested and re-suspended in chilled PBS/1% FCS, then mixed with phycoerythrin (PE) or FITC-conjugated antibodies specific for CD1a, CD209, human leukocyte antigen (HLA)-ABC, HLA-DR, CD80, CD86, CD38, CD40, CD25, CD123, CD83, CCR6, CCR7, CD70, and CD14; isotype-matched antibodies were used as controls. After thorough washing, fluorescence analysis was performed with a LSRII flow cytometer (BD Biosciences™) and FlowJo software (Treestar). Chemotaxis of DCs was measured by migration through a 8-μm pore size polycarbonate filter. IL-10 and IL-12 concentrations in the DC supernatants were determined using ELISA.

Example 2

AGS-003 Produces Treg Effector Cells

In Argos Therapeutics, Inc.'s clinical trial ("ADAPT trial"), renal cell carcinoma (RCC) patients were treated with the autologous dendritic cell therapy AGS-003 essentially as described in Amin et al. (2015) *J. Immunother. Cancer* 3:14. The effects of this therapy on populations of patient T cells were monitored using multi-color flow cytometry to assess expression of a variety of cell surface phenotype markers including CD3, CD4, CD25, CD127, and intracellular expression of markers including FoxP3.

Patient PBMCs obtained from the patient prior to treatment with AGS-003 were cultured in vitro with AGS-003 and then assessed using multi-color flow cytometry. Data presented below show that while the patient PBMCs collected prior to any treatment contain regulatory T cells ("Tregs"), upon in vitro culturing with AGS-003 DC product, Treg effector (Treg/eff) cells are produced. Treg effector cells differ from "classic" Tregs by the expression of PD-1 and lack of CXCR4 expression. Furthermore, stimulation of patient PBMCs in vitro with AGS-003 DC product induces proliferation of Treg effector cells and not classic Treg cells.

Study of T cells in ADAPT patients. T regulatory cells with suppressor activity are CD3+/CD4+/CD25+/CD127−/FoxP3+. FoxP3 expression can also be an early activation marker for CD3 T cells with pro-inflammatory effector function, so while the invention is not limited by any particular mechanism of action, it is possible that in vivo administration of AGS-003 could shift the function of FoxP3+ Treg cells from suppressor function to pro-inflammatory function. Data gathered from patients treated with AGS-003 suggests that FoxP3+ Treg/eff cells proliferate when cultured in vitro with AGS-003 dendritic cells (DCs). These AGS-003-induced Treg/eff cells differ from "classic" Tregs by the positive expression of PD-1 and negative (i.e., lack of) expression of the chemokine receptor CXCR4. Thus, the designation "Treg/eff" is used herein to identify a novel population of activated CD4+/FoxP3+/PD-1+/CXCR4− T cells that can proliferate after culture with AGS-003 DCs.

Methods to determine number of T regulatory cells in peripheral whole blood collections. A small volume of whole blood was collected in heparin sulphate tubes and stained with a cocktail of fluorochrome-conjugated antibodies including anti-CD3, anti-CD25, anti-CD4 and anti-CD127 antibodies. After staining, red blood cells were lysed and labeled cells were fixed and permeablized. Intracellular FoxP3 expression was detected in permeablized cells using a fluorescently conjugated anti-FoxP3 antibody. Labeled cells were added to Trucount bead tubes (BD Biosciences) in a fixed volume and cellular events collected on a flow cytometer. The number of Treg cells are expressed as number of cells/100 microliters of whole blood.

Methods to determine number of T regulatory cells in in vitro PBMC cultures. After in vitro culture, PBMCs were stained with a cocktail of fluorochrome conjugated antibodies containing anti-CD3, anti-CD25, anti-CD4 and anti-CD127 antibodies. Additional conjugated antibodies could be added to the cocktail to stain other cell surface markers (e.g., anti-PD-1 and anti-CXCR4). Cells were then fixed and permeabilized and expression of FoxP3 was detected using a fluorescently-conjugated anti-FoxP3 antibody. Additional conjugated antibodies such as anti-Ki67 could be added to the fix/permeablized cells to measure the number of proliferating cells (see, e.g., data shown in FIG. 3). Labeled cells were added to Trucount bead tubes (BD Biosciences®) in a fixed volume and cellular events collected on a flow cytometer. The number of T regulatory cells were expressed as number of cells/mL of culture.

Figure 1:
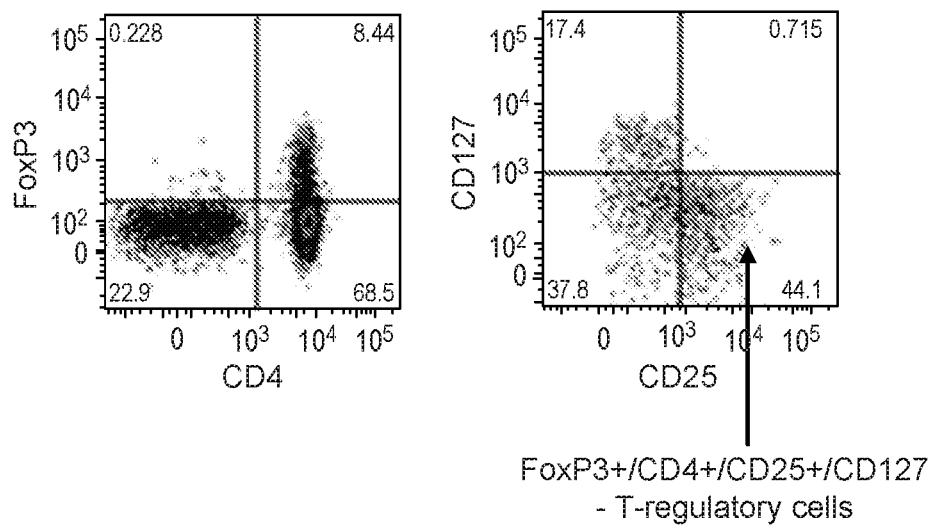
FIG. 1 shows a multi-color flow cytometry gating strategy to identify T regulatory cells ("Tregs") in whole blood. The left panel shows CD3+ T cells gated by FoxP3 (y-axis) and CD4 (x-axis) expression. Cells identified as FoxP3+ and CD4+(left panel, upper right quadrant) were further gated as shown in the right panel for expression of CD127 (y-axis) and CD25 (x-axis), so that FoxP3+/CD4+/CD25+/CD127− Treg cells are quantified in the lower right quadrant of the right panel. The number of T regulatory cells are determined using Trucount bead tubes (BD Biosciences). The numbers shown in each corner of the left and panels indicate the percentage of cells in that quadrant defined by the internal lines. Because the right panel shows the further gating of cells identified as FoxP3+ and CD4+ in the left panel, the percentage of FoxP3+/CD4+/CD25+/CD127− Treg cells in the original population of cells can be calculated as 44.1% of 8.44%, or 3.72%.

Gating strategy to identify T regulatory cells in whole blood. FIG. 1 shows a multi-color flow cytometry gating strategy to identify T regulatory cells in whole blood. CD3+ T cells were gated to identify FoxP3+ and CD4+ cells, which were then further gated to identify CD25+ and CD127− cells to quantify the population of FoxP3+/CD4+/CD25+/CD127− Treg cells. The number of T regulatory cells were determined using Trucount bead tubes (BD Biosciences®) and expressed as number of cells/100 microliters of whole blood.

In vitro detection of Foxp3+/CD25+ Treg subsets by PD-1 and CXCR4 expression (data shown in FIG. 2). PBMCs were collected from a patient in the ADAPT clinical trial at visit 2 (prior to the administration of AGS-003) and visit 12 (following administration of seven doses of AGS-003) and were cultured for six days in Xvivo media containing 10% AB serum. No additional stimuli were added to the cultures. On day 6, PBMC cultures were stained for flow cytometry to determine the number of activated FoxP3+/CD25+/CD4+ T cells. First, CD4+ T cells were gated to identify CD25+/CD45RA− T cells, and these cells were then gated to determine expression of PD-1 and the level of CD4 expression to distinguish Treg from Treg/eff cells. Treg cells were identified as CD4 low-expressing, PD-1− cells, while Treg/eff cells were identified as CD4 high-expressing, PD-1+ cells. Each of these Treg and Treg/eff populations were then subgated by expression of FoxP3 and CXCR4. The data (presented in FIG. 1) showed that Treg/eff cells identified as PD-1+, CD4 high-expressing, and FoxP3+ are CXCR4 negative, and Treg cells identified as PD-1−, CD4 low-expressing, and FoxP3+ are CXCR4 positive. Thus, this gating strategy defined two FoxP3+ cell subsets: Treg/effs (Foxp3+/PD-1+ CXCR4−) and Tregs (Foxp3+/PD-1− CXCR4+). In this manner, classic Treg cells and Treg/eff cells are differentiated by the combinatorial expression of PD-1 and CXCR4: classic Treg cells are PD-1−/CXCR4+ and Treg effector cells are PD-1+/CXCR4−. These data also show that in vivo administration of AGS-003 DC product can increase the numbers of Treg effector cells after in vitro culture expansion.

CD4+/PD-1+ FoxP3+ T cells (Treg/eff cells) proliferate in vitro when stimulated with AGS-003 DC product (data shown in FIG. 3). PBMCs collected from an ADAPT trial patient at visit 1 (baseline) were cultured for six days in Xvivo media containing 10% AB serum at a 10:1 ratio with autologous AGS-003 DC product. Flow cytometry was used to identify Treg/eff cells (CD4+CD25+PD-1+ FoxP3+), and then cells were stained with the cell cycle marker Ki67 to examine proliferation. As shown in FIG. 3, Treg/eff cells were positive for Ki67, indicating proliferation. In contrast, the Treg cells (CD4 lo/CD25+/PD-1−/FoxP3+) mostly showed lack of staining for expression of Ki67, indicating that they were not proliferating. Thus, cocultivation of patient cells with AGS-003 DC product induced proliferation of Treg/eff cells but not of Treg cells.

FIG. 4 shows that in vitro culture of PBMCs with AGS-003 DC autologous product produces concurrent expansion of Treg/eff cells and CTLs. PBMCs were collected from 15 clinical trial ("ADAPT") subjects at baseline and cultured in vitro with autologous AGS-003 DC product for 6 days. On day 6, the number of lytic CTLs (CD3+/CD8+/CD25+/CD45RA−/GrB+ cells) were determined and plotted versus the number of Treg/eff cells (CD3+/CD4+/CD25+ CD45RA−/PD-1+/Foxp3+ cells; see FIG. 4). A statistically significant association was detected between the number of CTLs and Treg/eff cells in the cultures ($\rho=0.59$, $p<0.0208$). Thus, while the invention is not limited to or bound by any particular mechanism of action, it is possible that the AGS-003 DC product stimulates an immune response at least in part by causing the expansion of both CTLs and Treg/effs.

What is claimed:

1. A method for treating a cancer patient with a dendritic cell vaccine comprising the steps of:
   a) obtaining a count of the regulatory T cells (Tregs) per unit volume in the blood of said patient;
   b) confirming that said count exceeds a treatment threshold value of Tregs per unit volume; and
   c) administering said dendritic cell vaccine to said patient, wherein said treatment threshold value exceeds 500 Tregs/100 microliters of whole blood or an equivalent measurement.

2. The method of claim 1, wherein said dendritic cell vaccine comprises PME-CD40L mature dendritic cells (DCs) that are loaded with an antigen.

3. The method of claim 2, wherein said DCs are loaded with said antigen by transfection with RNA encoding said antigen.

4. The method of claim 3, wherein said RNA is prepared from cancer cells of said patient.

5. The method of claim 1, wherein said Tregs are identified as CD4+, CD25+, and one of FoxP3+ or CD127−.

6. The method of claim 1, wherein said Tregs are identified as CD4+, CD25+, FoxP3+, and CD127−.

7. The method of claim 1, wherein said treatment threshold value exceeds 650 Tregs/100 microliters of whole blood or an equivalent measurement.

8. A method of determining whether an immune response was induced in a patient by a treatment, comprising the steps of:
   a) quantifying the number of regulatory T cells (Tregs) and/or Treg effector cells (Treg/eff cells) present in a sample of a patient's blood to establish a baseline reading;
   b) following administration to said patient of a treatment, quantifying the number of Tregs and/or Treg/eff cells present in the sample of said patient's blood to establish a post-treatment reading;
   c) comparing said baseline reading and said post-treatment reading to determine whether the frequency or amount of Tregs and/or Treg/eff cells present in the sample of the patient's blood has increased;
   wherein a significant decrease in the frequency or amount of Tregs and/or a significant increase in the frequency or amount of Treg/eff cells indicates that the immune response was induced in the patient, wherein said patient is selected for the treatment by:
   a) obtaining a count of the Trees per unit volume in the blood of said patient; and
   b) confirming that said count exceeds a treatment threshold value of Tress per unit volume,
   wherein said treatment threshold value exceeds 500 Tregs/100 microliters of whole blood or an equivalent measurement.

9. The method of claim 8, wherein said treatment comprises administering to said patient autologous mature DCs prepared in vitro.

10. The method of claim 8, wherein said treatment comprises administering to said patient a dendritic cell vaccine which comprises PME-CD40L mature DCs that are loaded with an antigen.

11. The method of claim 8, wherein said Tregs are identified as CD4+, CD25+, and one of FoxP3+ or CD127−.

12. The method of claim 8, wherein said Tregs are identified as CD4+, CD25+, FoxP3+, and CD127−.

13. The method of claim 8, wherein said treatment threshold value exceeds 650 Tregs/100 microliters of whole blood or an equivalent measurement.

14. A method for administering a dendritic cell vaccine to a patient comprising the steps of:
   a) obtaining a count of the regulatory T cells (Tregs) per unit volume in the blood of said patient;
   b) confirming that said count exceeds a treatment threshold value of Tregs per unit volume; and
   c) administering said dendritic cell vaccine to said patient, wherein said treatment threshold value exceeds 500 Tregs/100 microliters of whole blood or an equivalent measurement.

15. The method of claim 14, wherein said dendritic cell vaccine comprises PME-CD40L mature dendritic cells (DCs) that are loaded with an antigen.

16. The method of claim 15, wherein said DCs are loaded with said antigen by transfection with RNA encoding said antigen.

17. The method of claim 16, wherein said RNA is prepared from cancer cells of said patient.

18. The method of claim 14, wherein said Tregs are identified as CD4+, CD25+, and one of FoxP3+ or CD127−.

19. The method of claim 14, wherein said Tregs are identified as CD4+, CD25+, FoxP3+, and CD127−.

20. The method of claim 14, wherein said treatment threshold value exceeds 650 Tregs/100 microliters of whole blood or an equivalent measurement.

* * * * *